(12) United States Patent
Kaper et al.

(10) Patent No.: US 10,017,759 B2
(45) Date of Patent: Jul. 10, 2018

(54) LIBRARY PREPARATION OF TAGGED NUCLEIC ACID

(71) Applicant: Illumina, Inc., San Diego, CA (US)

(72) Inventors: Fiona Kaper, San Diego, CA (US); Gordon Cann, Hayward, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 14/749,562

(22) Filed: Jun. 24, 2015

(65) Prior Publication Data

US 2015/0376608 A1 Dec. 31, 2015

Related U.S. Application Data

(60) Provisional application No. 62/017,786, filed on Jun. 26, 2014, provisional application No. 62/027,198, filed on Jul. 21, 2014.

(51) Int. Cl.
*C12N 15/10* (2006.01)

(52) U.S. Cl.
CPC ..... *C12N 15/1065* (2013.01); *C12N 15/1093* (2013.01); *C12N 15/1003* (2013.01)

(58) Field of Classification Search
CPC ............ C12N 15/1065; C12N 15/1093; C12Q 1/6806
See application file for complete search history.

(56) References Cited

U.S. PATENT DOCUMENTS

| | | | |
|---|---|---|---|
| 2004/0038213 A1* | 2/2004 | Kwon | C12Q 1/6806 435/6.11 |
| 2006/0188892 A1 | 8/2006 | Latham et al. | |
| 2010/0120098 A1* | 5/2010 | Grunenwald | C12N 15/10 435/91.2 |
| 2013/0065223 A1* | 3/2013 | Klein | C12Q 1/6806 435/5 |
| 2014/0194324 A1 | 7/2014 | Gormley et al. | |
| 2014/0228255 A1* | 8/2014 | Hindson | C12Q 1/6876 506/26 |
| 2015/0353989 A1 | 12/2015 | Fraser et al. | |
| 2016/0115474 A1 | 4/2016 | Jelinek et al. | |
| 2016/0208323 A1 | 7/2016 | Bernstein et al. | |

FOREIGN PATENT DOCUMENTS

| | | | |
|---|---|---|---|
| EP | 0611157 A2 | 8/1994 | |
| GB | 1410196.8 | 6/2015 | |
| GB | 1412207.1 | 6/2015 | |
| WO | 2010/048605 A1 | 4/2010 | |
| WO | 2011/026194 A1 | 3/2011 | |
| WO | WO 2012106546 A2 * | 8/2012 | ......... C12N 15/1093 |
| WO | WO 2013131962 A1 * | 9/2013 | ........... C12Q 1/6806 |
| WO | WO 2015189588 A1 * | 12/2015 | .............. C12P 19/34 |
| WO | WO 2016/0123692 A1 | 8/2016 | |

OTHER PUBLICATIONS

Entry for EC 3.4.21.62, IUBMB Enzyme Nomenclature, printed from http://www.chem.qmul.ac.uk/iubmb/enzyme/EC3/4/21/62.html, as pp. 1/2-2/2 on Aug. 3, 2016.*
Jacobs et al. Cloning, sequencing and expression of subtilisin Carlsberg from Bacillus licheniformis. Nucleic Acids Research, vol. 13, No. 24, pp. 8913-8928, 1985.*
Bryan, PN. Protein engineering of subtilisin. Biochimica et Biophysica Acta, vol. 1543, pp. 203-222, 2000.*
Nextera™ DNA Sample Prep Kit (Illumina®-Compatible), Cat. Nos. GA09115, GA091120, GA0911-50, GA0911-96, and GABC0950, www.epicentre.com, Lit. #307, Jun. 2011, pp. 1-12.*
QIAGEN Genomic DNA Handbook, QIAGEN, Aug. 2001, pp. 1 and 13.*
Greene et al. Urea and guanidine hydrochloride denaturation of ribonuclease, lysozyme, alpha-chymotripsin, and beta-lactoglobulin. The Journal of Biological Chemistry, vol. 249, No. 17, pp. 5388-5393, 1974.*
Kishore et al. Thermal, chemical and pH induced denaturation of a multimeric beta-galactosidase reveals multiple unfolding pathways. PLOS ONE, vol. 7, No. 11, e50380, Nov. 2012, printed as pp. 1/9-9/9.*
Rowland et al. Tn552 transposase purification and in vitro activities. The EMBO Journal, vol. 14, No. 1, pp. 196-205, 1995.*
Stahlberg et al. Single-cell gene expression profiling using reverse transcrption quantitative real-time PCR. Methods, vol. 50, pp. 282-288, 2010.*
Bengtsson et al. Quantification of mRNA in single cells and modelling of RT-qPCR induced noise. BMC Molecular Biology, vol. 9, 63, Jul. 2008, printed as p. 1/11-11/11.*
Adey et al. Rapid, low-input, low-bias construction of shotgun fragment libraries by high-density in vitro transposition. Genome Biology, vol. 11, R119, 2010, printed as pp. 1/17-17-17.*
Lin et al. Highly-efficient colony PCR methods for red yeasts and its application to identify mutations within two leucine auxotroph mutants. Yeast, vol. 29, pp. 467-474, Oct. 2012.*
Proteinase K, recombinant, PCR Grade, Roche, Lot. No. 11469400, Mar. 2011, Roche (Cat. No. 03 115 887 001, Cat. No. 03 115 828 001, and Cat. No. 03 115 844 001 product information sheet, version Nov. 2005, printed as pp. 1/2-2/2.*
Enzyme entry 3.4.21.64, Peptidase K, https://enzyme.expasy.org/EC/3.4.21.64, printed on Mar. 7, 2018 as p. 1/1. (Year: 2018).*
Prosite documentation PDOC00125, SErine proteases, subtilase family, active sites, https://prosite.expasy.org/PDOC000125, printed on Mar. 7, 2018 as pp. 1/3-3/3. (Year: 2018).*
Enzyme entry 3.4.21.62, Subtilisin, https://enzyme.expasy.org/EC/3.4.21.62, printed on Mar. 7, 2018 as pp. 1/2-2/2. (Year: 2018).*
Subtilisin 3.4.21.62, Enzyme Handbook. Spinger-Verlag Berlin Heidelberg 1998, pp. 1-2. (Year: 1998).*
UniProtKB results for ec:3.4.21.62, http://www.uniprot.org/uniprot/?query=reviewed:yes%20and%20ec:3.4.21.62, printed on Mar. 7, 2018 as p. 1/1. (Year: 2018).*

(Continued)

*Primary Examiner* — Jennifer Dunston
(74) *Attorney, Agent, or Firm* — Mueting, Raasch & Gebhardt, P.A.

(57) ABSTRACT

A method of preparing a library of tagged nucleic acid fragments including contacting a population of cells directly with a lysis reagent having one or more protease to generate a cell lysate; inactivating the protease to generate an inactivated cell lysate, and applying a transposase and a transposon end composition containing a transferred strand to the inactivated cell lysate under conditions wherein the target nucleic acid and the transposon end composition undergo a transposition reaction.

23 Claims, 26 Drawing Sheets

(56) References Cited

OTHER PUBLICATIONS

GenBank Accession No. AEW87409.1, publicly available Jan. 2014, printed as pp. 1/2-2/2. (Year: 2014).*
GenBank Accession No. BAA06157.1, publicly available Feb. 2005, printed as pp. 1/2-2/2. (Year: 2005).*
National Center for Biotechnology Information. PubChem Substance Database; SID=49873558, https://pubchem.ncbi.nlm.nih.gov/substance/49873558 (accessed Mar. 15, 2018), publicly available 2008. (Year: 2008).*
Siezen et al. Subtilases: The superfamily of subtilisin-like serine proteases. Protein Science, vol. 6, pp. 5010-523, 1997. (Year: 1997).*
Chen et al., "Single-cell whole-genome analyses by Linear Amplification via Transposon Insertion (LIANTI)", *Science*, Apr. 14, 2017; 356(6334):189-194.
Chen et al., "Supplementary Materials for Single-cell whole-genome analyses by Linear Amplification via Transposon Insertion (LIANTI)", *Science*, Apr. 14, 2017; 356(6334):1-38.
Gole et al., "Massively parallel polymerase cloning and genome sequencing for single cells using nanoliter micowells", *Nature Biotechnology*, Dec. 2013; 31(12):1126-1134.
"Guidelines for PCR Optimization with Taq DNA Polymerase," *New England BioLabs Inc.*, Retrieved on Sep. 12, 2017 from the Internet: https://www.neb.com/tools-and-resources/usage-guidelines/guidelines-for-pcr-optimization-with-taq-dna-polymerase; 2 pgs.
"Nextera DNA Library Prep Reference Guide," *Illumina*, Document #15027987 v01; Jan. 2016, 1-36 pgs.

\* cited by examiner

LIBRARY PREPARATION OF TAGGED NUCLEIC ACID

CROSS-REFERENCE TO RELATED APPLICATIONS

This application claims priority to U.S. provisional application No. 62/017,786, filed Jun. 26, 2014; and U.S. provisional application No. 62/027,198, filed Jul. 21, 2014, each of which is incorporated herein by reference in its entirety.

SEQUENCE LISTING

The content of the following submission on ASCII text file is incorporated herein by reference in its entirety: a computer readable form (CRF) of the Sequence Listing, entitled 12957-171-999_SEQ_LIST.txt, of size 803 bytes, and created on Aug. 17, 2015.

FIELD

The present disclosure relates generally to methods for preparing a library of nucleic acid fragments, and more specifically to methods for preparing a library of nucleic acid fragments in a single tube using proteases for a variety of applications including, e.g., next generation DNA sequencing.

BACKGROUND

There are a variety of methods and applications for which it is desirable to generate a library of fragmented and tagged nucleic acid, e.g., for use as templates in DNA sequencing and/or for analysis of copy number variation.

Recently developed "next generation" DNA sequencing technologies, such as those developed by Illumina, Inc. (San Diego, Calif.), enable generating sequence data from up to millions of sequencing templates in a single sequence run using a massively parallel or multiplex format. This massively parallel nature of "next generation" sequencing requires generating libraries of nucleic acid fragments containing a collection or population of nucleic acid fragments from target nucleic acid sample, e.g., a genome DNA. More importantly, it requires that the combination of these nucleic acid fragments exhibits sequences that are qualitatively and/or quantitative representative of the sequence from the target nucleic acid sample. When nucleic acid sample is from cells, current methods for generating a library of nucleic acid fragments typically require a separate step for isolating target nucleic acid from cells, prior to nucleic acid fragmentation. This nucleic acid extraction step is usually wasteful of target nucleic acid sample, and usually renders the nucleic acid prepared unable to qualitatively represent the target nucleic acid from the sample. This becomes a particularly serious problem when the amount of sample is limited or difficult to obtain. To solve this problem, some current methods use nucleic acid amplification prior to fragmentation. However, amplification cannot ensure the representativeness of the target nucleic acid since the target nucleic acid is still partially lost during extraction prior to amplification.

Thus, there exists a need for new methods that enable rapid and efficient preparation of nucleic acid fragment library. The present disclosure addresses this need by providing methods for preparing a library of nucleic acid fragments in a single reaction mixture, e.g., in a single tube, using proteases. Related advantages are provided as well.

SUMMARY

In one aspect, provided herein is a method of preparing a library of tagged nucleic acid fragments including (a) contacting a population of cells directly with a lysis reagent to generate a cell lysate, wherein the lysis reagent has one or more proteases, and wherein the cell lysate contains a target nucleic acid; (b) inactivating the one or more proteases to form an inactivated cell lysate, and (c) directly applying at least one transposase and at least one transposon end composition containing a transferred strand to the inactivated cell lysate under conditions where the target nucleic acid and the transposon end composition undergo a transposition reaction to generate a mixture, wherein (i) the target nucleic acid is fragmented to generate a plurality of target nucleic acid fragments, and (ii) the transferred strand of the transposon end composition is joined to 5' ends of each of a plurality of the target nucleic acid fragments to generate a plurality of 5' tagged target nucleic acid fragments.

In some embodiments, steps (a), (b), and (c) provided herein are performed in a single reaction mixture, e.g., in a tube. In some embodiments, the population of cells is a minimal population of cells. In some embodiments, the minimal population of cells contains one, two, three, four, or five cells.

In some embodiments, the one or more proteases are selected from a group consisting of serine proteases, threonine proteases, cysteine proteases, aspartate proteases, glutamic acid proteases, and metalloproteases. In some embodiments, the one or more proteases are subtilisins and variants thereof. In some embodiments, the concentration of one or more proteases in the cell lysate is 0.1 mg/ml to 10 mg/ml. In some embodiments, the concentration of the one or more proteases in the cell lysate is 0.1 mg/ml to 2.5 mg/ml. In some embodiments, the concentration of the one or more proteases in the cell lysate is 0.5 mg/ml. In some embodiments, the concentration of the one or more proteases in the cell lysate is 4.5 mAU/ml to 500 mAU/ml. In some embodiments, the concentration of the one or more proteases in the cell lysate is 22.5 mAU/ml.

In some embodiments, the population of cells are contacted with the lysis reagent at pH 7.0 to pH 10.0 in step (a). In some embodiments, the population of cells are contacted with the lysis reagent at pH 7.0 to pH 9.0.

In some embodiments, the one or more proteases are inactivated by increasing temperature in step (b). In some embodiments, the one or more proteases are inactivated by increasing temperature to 50° C.-80° C. In some embodiments, the one or more proteases are inactivated by increasing temperature to 70° C. In some embodiments, the one or more proteases are inactivated by adding one or more inhibitors of the one or more proteases.

In some embodiments, the lysis reagent includes one or more detergents. In some embodiments, the one or more detergents are nonionic detergents. In some embodiments, the one or more detergents include TRITON.

In some embodiments, the target nucleic acid is a double-stranded DNA, and wherein the target nucleic acid remains the double-stranded DNA prior to applying a trasposease and a trasposon end composition in step (c). In some embodiments, the target nucleic acid is genomic DNA. In some embodiments, the target nucleic acid contains chromosomal DNA or a fragment thereof. In some embodiments, the target nucleic acid includes a genome or a partial genome.

In some embodiments, the at least one transposase is a Tn5 transposase. In some embodiments, the at least one transposon end composition includes Tn5 transposon end.

In some embodiments, the transferred strand includes tag domains containing one or more of a restriction site domain, a capture tag domain, a sequencing tag domain, an amplification tag domain, a detection tag domain, and an address tag domain.

In some embodiments, the method provided herein further includes (d) incubating the mixture from step (c) directly with at least one nucleic acid modifying enzyme under conditions wherein a 3' tag is joined to the 5' tagged target nucleic acid fragments to generate a plurality of di-tagged target nucleic acid fragments. In some embodiments, steps (a), (b), (c), and (d) are performed in a single reaction tube.

In some embodiments, the nucleic acid modifying enzyme is a polymerase and wherein said 3' tag is formed by extension of the 3' end of the 5' tagged target nucleic acid fragment. In some embodiments, the nucleic acid modifying enzyme is a ligase and wherein the 3' tag is formed by ligation of an oligonucleotide to the 3' end of the 5' tagged target nucleic acid fragment.

In some embodiments, the method provided herein further includes (e) amplifying one or more di-tagged target nucleic acid fragments to generate a library of tagged nucleic acid fragments with additional sequence at 5' end and/or 3' end of the di-tagged nucleic acid fragments. In some embodiments, steps (a), (b), (c), (d), and (e) are performed in a single reaction tube.

In some embodiments, the amplifying includes use of one or more of a polymerase chain reaction (PCR), a strand-displacement amplification reaction, a rolling circle amplification reaction, a ligase chain reaction, a transcription-mediated amplification reaction, or a loop-mediated amplification reaction. In some embodiments, the amplifying includes a PCR using a single primer that is complementary to the 3' tag of the di-tagged target DNA fragments. In some embodiments, the amplifying includes a PCR using a first and a second primer, wherein at least a 3' end portion of the first primer is complementary to at least a portion of the 3' tag of the di-tagged target nucleic acid fragments, and wherein at least a 3' end portion of the second primer exhibits the sequence of at least a portion of the 5' tag of the di-tagged target nucleic acid fragments. In some embodiments, a 5' end portion of the first primer is non-complementary to the 3' tag of the di-tagged target nucleic acid fragments, and a 5' end portion of the second primer does not exhibit the sequence of at least a portion of the 5' tag of the di-tagged target nucleic acid fragments. In some embodiments, the first primer includes a first universal sequence, and/or wherein the second primer includes a second universal sequence.

In some embodiments, the method provided herein further includes sequencing the tagged nucleic acid fragments. In some embodiments, the sequencing of the tagged nucleic acid fragments includes use of one or more of sequencing by synthesis, bridge PCR, chain termination sequencing, sequencing by hybridization, nanopore sequencing, and sequencing by ligation. In some embodiments, the sequencing of the tagged nucleic acid fragments includes use of next generation sequencing.

In some embodiments, the method provided herein further includes analyzing copy number variation. In some embodiments, the method provided herein further includes analyzing single nucleotide variation.

In another aspect, the present disclosure provides a kit for preparing a library of tagged nucleic acid fragments including (a) a lysis reagent having one or more proteases, and (b) a transposition reaction composition having at least one transposase and at least one transposon end composition containing a transferred strand.

In some embodiments, the one or more proteases are selected from a group consisting of serine proteases, threonine proteases, cysteine proteases, aspartate proteases, glutamic acid proteases, and metalloproteases. In some embodiments, the one or more proteases are subtilisins and variants thereof. In some embodiments, the lysis agent includes one or more detergents. In some embodiments, the one or more detergents include TRITON.

In some embodiments, the at least one transposon end composition include a tag domain and a 3' portion comprising the transferred strand. In some embodiments, the tag domain includes one or more of a restriction site domain, a capture tag domain, a sequencing tag domain, an amplification tag domain, a detection tag domain, and an address tag domain. In some embodiments, the transposition reaction composition includes two or more transposon end compositions, each of the two or more transposon end compositions includes a transferred strand that differs by at least one nucleotide. In some embodiments, the transposase is a Tn5 transposase. In some embodiments, the transposon end composition includes a Tn5 transposon end.

In some embodiments, the kit provided herein further includes a polymerase. In some embodiments, the kit provided herein further includes a ligase.

In some embodiments, the kit provided herein further includes a reagent for an amplification reaction. In some embodiments, the reagent for the amplification reaction is a reagent for PCR. In some embodiments, the reagent for the amplification reaction includes at least one primer. In some embodiments, the at least one primer includes a 3' portion that exhibits the sequence of at least a portion of the transferred strand. In some embodiments, the at least one primer includes a 5' portion that contains a universal sequence.

In some embodiments, the kit provided herein further includes a size selection reagent. In some embodiments, the size selection reagent includes AMPURE XP beads. In some embodiments, the kit provided herein further includes a library normalization reagent.

In some embodiments, the kit provided herein further includes an apparatus having a solid surface. In some embodiments, the apparatus is a flow cell apparatus. In some embodiments, the solid surface includes a patterned surface suitable for immobilization of a molecule in an ordered pattern.

DETAILED DESCRIPTION

Figure 1:
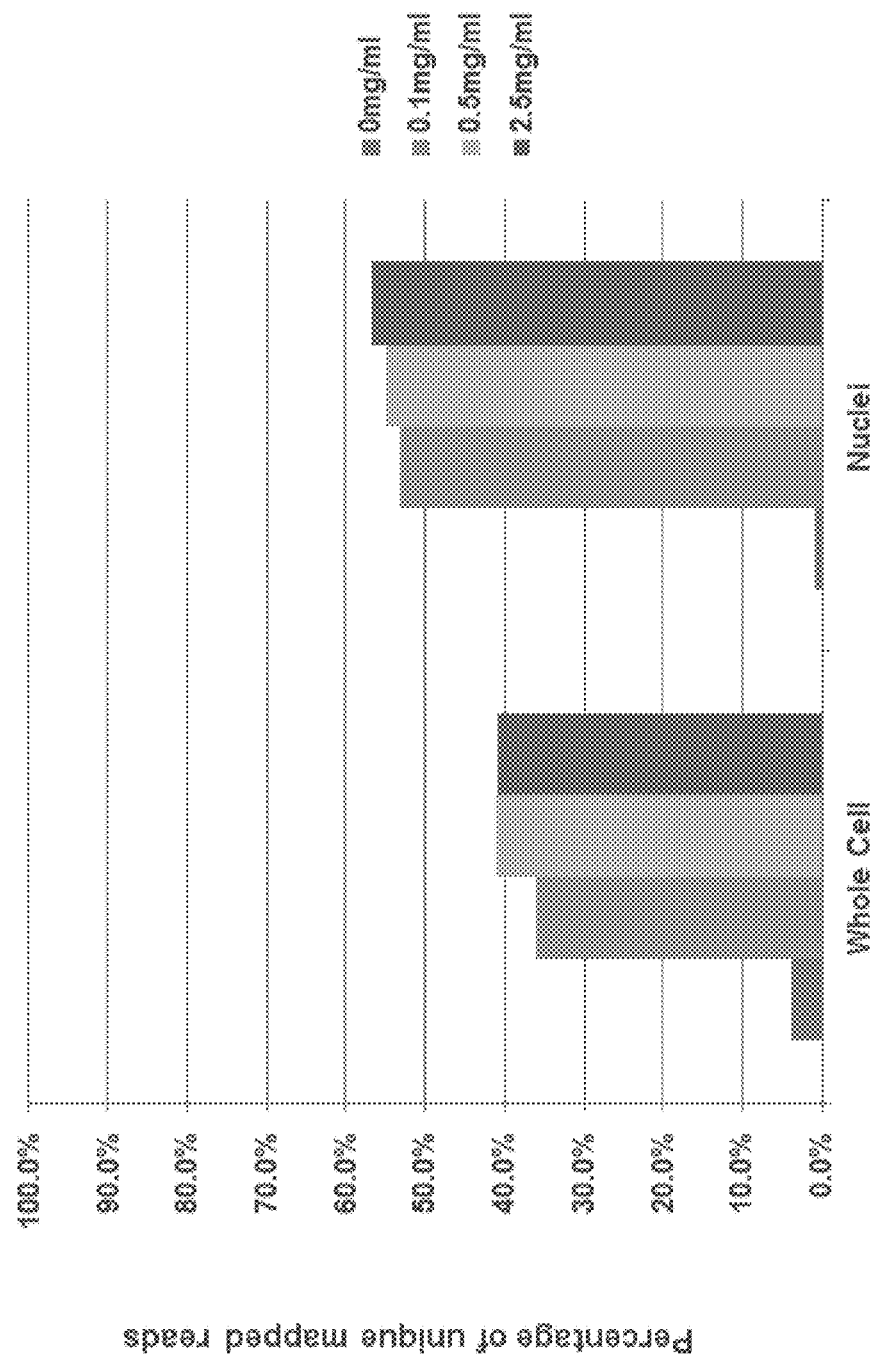
FIG. 1 is a histogram showing the percentage of unique mapped read in a sequencing using 0 mg/ml, 0.1 mg/ml, 0.5 mg/ml, or 2.5 mg/ml proteases treated whole cells or nuclei.

The present disclosure relates generally to methods for preparing a library of nucleic acid fragments, and more specifically to methods for preparing a library of nucleic acid fragments in a single reaction mixture, e.g., a single tube, using proteases for a variety of applications including, e.g., next generation sequencing.

Definitions

As used herein, the terms "includes," "including," "includes," "including," "contains," "containing," "have," "having," and any variations thereof, are intended to cover a non-exclusive inclusion, such that a process, method, product-by-process, or composition of matter that includes, includes, or contains an element or list of elements does not include only those elements but can include other elements not expressly listed or inherent to such process, method, product-by-process, or composition of matter.

As used herein, the terms "a" and "an" and "the" and similar referents in the context of describing the invention (especially in the context of the following claims) are to be construed to cover both the singular and the plural, unless otherwise indicated herein or clearly contradicted by context.

As used herein, the term "about" or "approximately" means within 5% of a given value or range.

As used herein, the term "a minimal population of cells" means a population of cells that contains an amount of DNA copies that is below nucleic acid sequencing capabilities absent a separation step such as DNA extraction prior to tagmentation. Exemplary separation steps include extracting DNA content from a cell lysate, and/or DNA amplification. A minimal population of cells can include one, two, three, four, or five cells. A minimal population of cells can be a single cell. "Nucleic acid sequencing capabilities," as used herein, means sequencing capability that can produce clean copy number variation data of a genome.

As used herein, the term "nucleic acid" means single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., H+, NH4+, trialkylammonium, tetraalkylammonium, Mg2+, Na+ and the like. A nucleic acid includes polynucleotide and oligonucleotide. A nucleic acid may be composed entirely of deoxyribonucleotides, entirely of ribonucleotides, or chimeric mixtures thereof. The nucleotide monomer units may include any of the nucleotides described herein, including, but not limited to, naturally occurring nucleotides and nucleotides analogs. Nucleic acid typically ranges in size from a few monomeric units, e.g, 5-40, to several thousands of monomeric nucleotide units. Nucleic acids include, but are not limited to, genomic DNA, cDNA, hnRNA, mRNA, rRNA, tRNA, fragmented nucleic acid, nucleic acid obtained from sub-cellular organelles such as mitochondria or chloroplasts, and nucleic acid obtained from microorganisms or DNA or RNA viruses that may be present on or in a biological sample.

As used herein, the term "target nucleic acid" is intended to mean a nucleic acid that is the object of an analysis or action. The analysis or action includes subjecting the nucleic acid to copying, amplification, sequencing and/or other procedure for nucleic acid interrogation. A target nucleic acid can include nucleotide sequences additional to the target sequence to be analyzed. For example, a target nucleic acid can include one or more adapters, including an adapter that functions as a primer binding site, that flank(s) a target nucleic acid sequence that is to be analyzed. A target nucleic acid hybridized to a capture oligonucleotide or capture primer can contain nucleotides that extend beyond the 5' or 3' end of the capture oligonucleotide in such a way that not all of the target nucleic acid is amenable to extension.

As used herein, the terms "isolate" and "purify" as used herein, refer to the reduction in the amount of at least one contaminant (such as protein and/or nucleic acid sequence) from a sample or from a source from which the material is isolated or purified.

As used herein, the term "size selection" means a procedure during which a sub-population of nucleic acid fragments, majority of which have a number of nucleotides falling in a defined range, is selected from a population of nucleic acid fragments, and thus the percentage of nucleic acid fragments having a number of nucleotides falling in the defined range increases.

As used herein, the term "protease" refers to a protein, polypeptide or peptide exhibiting the ability to hydrolyze polypeptides or substrates having a polypeptide portion. The protease(s) provided in the present methods can be a single protease possessing broad specificity. The present methods can use a mixture of various proteases. The proteases provided herein can be heat-labile and thus can be inactivated by heat. In certain embodiments, the proteases provided herein can be inactivated at a temperature above about 25° C., 30° C., 35° C., 40° C., 45° C., 50° C., 55° C., 60° C., 65° C., 70° C., 75° C., 80° C. or above about 85° C. The proteases provided herein can digest chromatin proteins and other DNA-binding proteins to release naked genomic DNA, and can also digest endogenous DNase to protect DNA from degradation. The proteases provided herein include, but not limited to, serine proteases, threonine proteases, cysteine proteases, aspartate proteases, glutamic acid proteases, and metalloproteases. Typically, aspartic, glutamic and metallo proteases activate a water molecule which performs a nucleophilic attack on the peptide bond to hydrolyze it. Serine, threonine and cysteine proteases typically use a nucleophilic residue to perform a nucleophilic attack to covalently link the protease to the substrate protein, releasing the first half of the product. This covalent acyl-enzyme intermediate is then hydrolyzed by activated water to complete catalysis by releasing the second half of the product and regenerating the free enzyme. Exemplary protease used herein includes a serine protease isolated from a recombinant *Bacillus* strain. Exemplary proteases used herein include subtilisin and variants thereof, including subtilisin Carlsberg, ALCALASE, and subtilisin S41. Subtilisins and variants thereof are known to those of skill in the art and include, for example ALCALASE, ALCALASE 0.6L, ALCALASE 2.5L, ALK-enzyme, bacillopeptidase A, bacillopeptidase B, *Bacillus subtilis* alkaline proteinase bioprase, bioprase AL 15, bioprase APL 30, colistinase, subtilisin J, subtilisin S41, subtilisin Sendai, subtilisin GX, subtilisin E, subtilisin BL, GENENASE I, ESPERASE, MAXATASE, thermoase PC 10, protease XXVII, thermoase, SUPERASE, subtilisin Carlsberg subtilisin DY, subtilopeptidase, SP 266, SAVINASE 8.0L, SAVINASE 4.0T, KAZUSASE, protease VIII, OPTICLEAN, protin A 3L, SAVINASE, SAVINASE 16.0L, SAVINASE 32.0L EX, orientase 10B, protease S, serine endopeptidase. In particular embodiments of the methods and compositions presented herein, a heat-labile protease such as subtilisin and heat-labile variants of subtilisin can be used, as represented by the exemplary disclosure of Davail et al., 1994, *J. Biol. Chem.*, 26:17448-17453, which is incorporated herein by reference in its entirety.

As used herein, the term "protease inhibitor" refers to a substance, e.g., a compound, capable of at least partially reducing the ability of a protease to hydrolyze peptides.

As used herein, the term "ligase" refers to a nucleic acid modifying enzyme that catalyzes intra- and intermolecular formation of phosphodiester bonds between 5'-phosphate and 3'-hydroxyl termini of nucleic acid strands. Ligases include, e.g., template-independent ligases, such as CIRCLIGASE™ ssDNA ligase, that can join ends of single-stranded RNA and DNA, and template-dependent, that seal nicks in double-stranded DNA. As used herein, "template-dependent ligase" means a DNA ligase that catalyzes intra- and intermolecular formation of phosphodiester bonds between 5'-phosphate and 3'-hydroxyl termini of DNA strands that are adjacent to each other when annealed to a complementary polynucleotide. The polynucleotide to which both of the DNA ends to be ligated anneal adjacently is referred to herein as a "ligation template" and the ligation is referred to as "template-dependent ligation." The ligation template can be a complementary DNA sequence in genomic or other DNA in a biological sample, or the ligation template can be a "bridging oligodeoxyribonucleotide" or "ligation splint oligodeoxyribonucleotide" (or "ligation splint") that is synthesized and/or provided specifically for use in a particular assay or method. Examples template-dependent DNA ligases include NAD-type DNA ligases such as *E. coli* DNA ligase, Tth DNA ligase, Tfl DNA ligase, and AMPLIGASE® DNA ligase (EPICENTRE Biotechnologies, Madison, Wis., USA), which catalyze intramolecular ligation of ssDNA molecules only in the presence of a ligation template, and ATP-type DNA ligases, such as T4 DNA ligase or FASTLINK™ DNA ligase (EPICENTRE Biotechnologies).

As used herein, the term "tagmentation" refers to the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments. Additional sequences can be added to the ends of the adapted fragments, for example by PCR, ligation, or any other suitable methodology known to those of skill in the art. As used herein, the term "transposome complex" refers to a transposase enzyme non-covalently bound to a double stranded nucleic acid. For example, the complex can be a transposase enzyme preincubated with double-stranded transposon DNA under conditions that support non-covalent complex formation. Double-stranded transposon DNA can include, without limitation, Tn5 DNA, a portion of Tn5 DNA, a transposon end composition, a mixture of transposon end compositions or other double-stranded DNAs capable of interacting with a transposase such as the hyperactive Tn5 transposase.

As used herein, the term "transposition reaction" refers to a reaction wherein one or more transposons are inserted into target nucleic acids, e.g., at random sites or almost random sites. Essential components in a transposition reaction are a transposase and DNA oligonucleotides that exhibit the nucleotide sequences of a transposon, including the transferred transposon sequence and its complement (the non-transferred transposon end sequence) as well as other components needed to form a functional transposition or transposome complex. The DNA oligonucleotides can further include additional sequences (e.g., adaptor or primer sequences) as needed or desired. In some embodiments, the method provided herein is exemplified by employing a transposition complex formed by a hyperactive Tn5 transposase and a Tn5-type transposon end (Goryshin and Reznikoff, 1998, *J. Biol. Chem.*, 273: 7367) or by a MuA transposase and a Mu transposon end comprising R1 and R2 end sequences (Mizuuchi, 1983, *Cell*, 35: 785; Savilahti et al., 1995, *EMBO J.*, 14: 4893). However, any transposition system that is capable of inserting a transposon end in a random or in an almost random manner with sufficient efficiency to 5'-tag and fragment a target DNA for its intended purpose can be used in the present invention. Examples of transposition systems known in the art which can be used for the present methods include but are not limited to Staphylococcus aureus Tn552 (Colegio et al., 2001, *J Bacterid.*, 183: 2384-8; Kirby et al., 2002, *Mol Microbiol*, 43: 173-86), TyI (Devine and Boeke, 1994, *Nucleic Acids Res.*, 22: 3765-72 and International Patent Application No. WO 95/23875), Transposon Tn7 (Craig, 1996, *Science.* 271: 1512; Craig, 1996, Review in: *Curr Top Microbiol Immunol*, 204: 27-48), TnlO and ISlO (Kleckner et al., 1996, *Curr Top Microbiol Immunol*, 204: 49-82), Mariner transposase (Lampe et al., 1996, *EMBO J.*, 15: 5470-9), Tci (Plasterk, 1996, *Curr Top Microbiol Immunol*, 204: 125-43), P Element (Gloor, 2004, *Methods Mol Biol*, 260: 97-114), TnJ (Ichikawa and Ohtsubo, 1990, *J Biol Chem.* 265: 18829-32), bacterial insertion sequences (Ohtsubo and Sekine, 1996, *Curr. Top. Microbiol. Immunol.* 204:1-26), retroviruses (Brown et al., 1989, *Proc Natl Acad Sci USA,* 86: 2525-9), and retrotransposon of yeast (Boeke and Corces, 1989, *Annu Rev Microbiol.* 43: 403-34). The method for inserting a transposon end into a target sequence can be carried out in vitro using any suitable transposon system for which a suitable in vitro transposition system is available or that can be developed based on knowledge in the art. In general, a suitable in vitro transposition system for use in the methods provided herein requires, at a minimum, a transposase enzyme of sufficient purity, sufficient concentration, and sufficient in vitro transposition activity and a transposon end with which the transposase forms a functional complex with the respective transposase that is capable of catalyzing the transposition reaction. Suitable transposase transposon end sequences that can be used in the invention include but are not limited to wild-type, derivative or mutant transposon end sequences that form a complex with a transposase chosen from among a wild-type, derivative or mutant form of the transposase.

As used herein, the term "transposase" refers to an enzyme that is capable of forming a functional complex with a transposon end-containing composition (e.g., transposons, transposon ends, transposon end compositions) and catalyzing insertion or transposition of the transposon end-containing composition into the double-stranded target nucleic acid with which it is incubated, for example, in an in vitro transposition reaction. A transposase as presented herein can also include integrases from retrotransposons and retroviruses. Transposases, transposomes and transposome complexes are generally known to those of skill in the art, as exemplified by the disclosure of US 2010/0120098, the content of which is incorporated herein by reference in its entirety. Although many embodiments described herein refer to Tn5 transposase and/or hyperactive Tn5 transposase, it will be appreciated that any transposition system that is capable of inserting a transposon end with sufficient efficiency to 5'-tag and fragment a target nucleic acid for its intended purpose can be used in the present invention. In particular embodiments, a transposition system is capable of inserting the transposon end in a random or in an almost random manner to 5'-tag and fragment the target nucleic acid.

As used herein, the term "transposon end" means a double-stranded DNA that exhibits only the nucleotide sequences (the "transposon end sequences") that are necessary to form the complex with the transposase or integrase enzyme that is functional in an in vitro transposition reaction. A transposon end forms a "complex" or a "synaptic complex" or a "transposome complex" or a "transposome composition with a transposase or integrase that recognizes and binds to the transposon end, and which complex is capable of inserting or transposing the transposon end into target DNA with which it is incubated in an in vitro transposition reaction. A transposon end exhibits two complementary sequences consisting of a "transferred strand" and a "non transferred strand." For example, one transposon end that forms a complex with a hyperactive Tn5 transposase (e.g., EZ-Tn5™ Transposase, EPICENTRE Biotechnologies, Madison, Wis., USA) that is active in an in vitro transposition reaction comprises a transferred strand that exhibits a "transferred transposon end sequence" as follows: 5' AGATGTGTATAAGAGACAG 3' (SEQ ID NO:1), and a non-transferred strand that exhibits a "non-transferred transposon end sequence" as follows: 5' CTGTCT CTTATACACATCT 3' (SEQ ID NO:2). The 3'-end of a transferred strand is joined or transferred to target nucleic acid in an in vitro transposition reaction. The non-transferred strand, which exhibits a transposon end sequence that is complementary to the transferred transposon end sequence, is not joined or transferred to the target nucleic acid in an in vitro transposition reaction.

As used herein, the term "transposon end composition" refers to a composition comprising a transposon end (the minimum double-stranded DNA segment that is capable of acting with a transposase to undergo a transposition reaction), optionally plus additional sequence or sequences. 5'-of the transferred transposon end sequence and/or 3'-of the non-transferred transposon end sequence. For example, a transposon end attached to a tag is a "transposon end composition."

As used herein, the term "transferred strand" refers to the transferred portion of both "transposon ends" and "transposon end compositions" (regardless of whether the transposon end is attached to a tag or other moiety). Similarly, the term "non-transferred strand" refers to the non-transferred portion of both "transposon ends" and "transposon end compositions."

As used herein, the term "tag" refers to a non-target nucleic acid component, generally DNA, that provides a means of addressing a nucleic acid fragment to which it is joined. For example, in some embodiments, a tag comprises a nucleotide sequence that permits identification, recognition, and/or molecular or biochemical manipulation of the DNA to which the tag is attached (e.g., by providing a site for annealing an oligonucleotide, such as a primer for extension by a DNA polymerase, or an oligonucleotide for capture or for a ligation reaction). The process of joining the tag to the nucleic acid molecule is sometimes referred to herein as "tagging" and the nucleic acid that undergoes tagging or that contains a tag is referred to as "tagged" (e.g., "tagged DNA").

As used herein, the term "tag domain" refers to a portion or domain of a tag that exhibits a sequence for a desired intended purpose or application. One tag domain is the "transposon end domain," which tag domain exhibits the transferred transposon end sequence. In some embodiments, the transferred strand also exhibits one or more other nucleotide sequences 5'-of the transferred transposon end sequence, the tag also has one or more other "tag domains" in the 5'-portion, each of which tag domains is provided for any desired purpose. For example, some embodiments contain a transposon end composition that includes a tag domain selected from among one or more of a restriction site tag domain, a capture tag domain, a sequencing tag domain, an amplification tag domain, a detection tag domain, an address tag domain, and a transcription promoter domain.

As used herein, the term "restriction site domain" refers to a tag domain that exhibits a sequence for the purpose of facilitating cleavage using a restriction endonuclease. For example, the restriction site domain can be used to generate di-tagged linear ssDNA fragments. The restriction site domain can also be used to generate a compatible double-stranded 5'-end in the tag domain so that this end can be ligated to another DNA molecule using a template-dependent DNA ligase.

As used herein, the term "capture tag domain" refers to a tag domain that exhibits a sequence for the purpose of facilitating capture of the nucleic acid fragment to which the tag domain is joined (e.g., to provide an annealing site or an affinity tag for a capture of the di-tagged linear ssDNA fragments on a bead or other surface, e.g., wherein the annealing site of the tag domain sequence permits capture by annealing to a specific sequence which is on a surface, such as a probe on a bead or on a microchip or microarray or on a sequencing bead). In some embodiments, the capture tag domain comprises a 5'-portion of the transferred strand that is joined to a chemical group or moiety that includes an affinity binding molecule (e.g., biotin, streptavidin, an antigen, or an antibody that binds the antigen, that permits capture of the di-tagged linear ssDNA fragments on a surface to which a second affinity binding molecule is attached that forms a specific binding pair with the first affinity binding molecule).

As used herein, the term "sequencing tag domain" refers to a tag domain that exhibits a sequence for the purposes of facilitating sequencing of the nucleic acid fragment to which the tag is joined (e.g., to provide a priming site for sequencing by synthesis, or to provide annealing sites for sequencing by ligation, or to provide annealing sites for sequencing by hybridization).

As used herein, the term "amplification tag domain" refers to a tag domain that exhibits a sequence for the purpose of facilitating amplification of a nucleic acid to which said tag is appended. For example, in some embodiments, the amplification tag domain provides a priming site for a nucleic acid amplification reaction using a DNA polymerase (e.g., a PCR amplification reaction or a strand-displacement amplification reaction, or a rolling circle amplification reaction), or a ligation template for ligation of probes using a template-dependent ligase in a nucleic acid amplification reaction (e.g., a ligation chain reaction).

As used herein, the term "detection tag domain" refers to a tag domain that exhibits a sequence or a detectable chemical or biochemical moiety for the purpose of facilitating detection of the tagged nucleic acid fragments (e.g., a visible, fluorescent, chemiluminescent, or other detectable dye; an enzyme that is detectable in the presence of a substrate, e.g., an alkaline phosphatase with NBT plus BCIP or a peroxidase with a suitable substrate; a detectable protein, e.g., a green fluorescent protein; and an affinity-binding molecule that is bound to a detectable moiety or that can form an affinity binding pair or a specific binding pair with another detectable affinity-binding molecule; or any of the many other detectable molecules or systems known in the art).

As used herein, the term "address tag domain" means a tag domain that exhibits a sequence that permits identification of a specific sample (e.g., wherein the transferred strand has a different address tag domain that exhibits a different sequence for each sample).

As used herein, the terms "amplify" or "amplified" "amplifying" as used in reference to a nucleic acid or nucleic acid reactions, refer to in vitro methods of making copies of a particular nucleic acid, such as a target nucleic acid, or a tagged nucleic acid. Numerous methods of amplifying nucleic acids are known in the art, and amplification reactions include, but not limited to, polymerase chain reactions, ligase chain reactions, strand displacement amplification reactions, rolling circle amplification reactions. The nucleic acid that is amplified can be DNA. The products resulting from amplification of a nucleic acid molecule or molecules ("amplification products"), whether the starting nucleic acid is DNA, RNA or both, can be either DNA or RNA, or a mixture of both DNA and RNA nucleosides or nucleotides, or they can include modified DNA or RNA nucleosides or nucleotides. A "copy" does not necessarily mean perfect sequence complementarily or identity to the target sequence. For example, copies can include nucleotide analogs such as deoxyinosine or deoxyuridine, intentional sequence alterations (such as sequence alterations introduced through a primer containing a sequence that is hybridizable, but not complementary, to the target sequence), and/or sequence errors that occur during amplification.

A as used herein, the term a "library of tagged nucleic acid fragments" refers to a collection or population of tagged nucleic acid fragments (e.g., di-tagged nucleic acid fragments) generated from a resource, e.g., whole genome, wherein the combination of the tagged nucleic acid fragments in the collection or population exhibits sequences that are qualitatively and/or quantitatively representative of the sequence of the resource from which the tagged nucleic acid fragments were generated, e.g., whole genome. It is possible that a library of tagged nucleic acid fragments does not contain a tagged nucleic fragment representing every sequence which is exhibited by the resource.

As used herein, the term "nucleic acid modifying enzyme" refers to any enzyme that acts upon nucleic acid, e.g., DNA, to effect a modification, e.g., cleavage, ligation, polymerization, phosphorylation, etc. Nucleic acid modifying enzymes include, e.g., polymerases, nucleases, transferases, ligases, phosphorylases, phosphatases, methylases, transosases, etc. "DNA modifying enzymes" include any enzymes that act on DNA, including enzymes that also act on other substrates, such as RNA.

As used herein, the term "DNA polymerase" refers to a modifying enzyme that catalyzes the polymerization of deoxyribonucleotides into a DNA strand. DNA polymerases include "template-dependent DNA polymerases," which require a template nucleic acid to determine the order in which deoxyribonucleotides are added in the polymer, or they may be "template-independent" such that they catalyze polymerization without reference to a template sequence. In addition to synthesizing DNA polymers, DNA polymerases may comprise other features or activities. For example, a DNA polymerase may be characterizes as having or lacking 5' to 3' exonuclease activity (also referred to a 5' exonuclease or 5' nuclease activity), 3' to 5' exonuclease activity, and strand displacement activity.

As used herein, the term "primer" is an oligonucleotide ("oligo"), generally with a free 3'-OH group that can be extended by a nucleic acid polymerase. For a template-dependent polymerase, generally at least the 3'-portion of the primer oligo is complementary to a portion of a template nucleic acid, to which the oligo "binds" (or "complexes," "anneals," or "hybridizes"), by hydrogen bonding and other molecular forces, to the template to give a primer/template complex for initiation of synthesis by a DNA polymerase, and which is extended by the addition of covalently bonded bases linked at its 3'-end which are complementary to the template in the process of DNA synthesis. The result is a primer extension product.

As used herein, the term "universal sequence" refers to a region of nucleotide sequence that is common to or shared by, two or more nucleic acid molecules. Optionally, the two or more nucleic acid molecules also have regions of sequence differences. Thus, for example, the 5' tags can comprise identical or universal nucleic acid sequences and the 3' tags can comprise identical or universal sequences. A universal sequence that may be present in different members of a plurality of nucleic acid molecules can allow the replication or amplification of multiple different sequences using a single universal primer that is complementary to the universal sequence.

As used herein, the terms "solid surface," "solid support" and other grammatical equivalents herein refer to any material that is appropriate for or can be modified to be appropriate for the attachment of a polynucleotide. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. In some embodiments, solid supports and solid surfaces are located within a flow cell apparatus. In some embodiments, the solid support comprises a patterned surface suitable for immobilization of transposome complexes in an ordered pattern. A "patterned surface" refers to an arrangement of different regions in or on an exposed layer of a solid support. In some embodiments, the solid support comprises an array of wells or depressions in a surface. The composition and geometry of the solid support can vary with its use. In some embodiments, the solid support is a planar structure such as a slide, chip, microchip and/or array. As such, the surface of a substrate can be in the form of a planar layer. In some embodiments, the solid support comprises one or more surfaces of a flowcell. The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference. In some embodiments, the solid support or its surface is non-planar, such as the inner or outer surface of a tube or vessel. In some embodiments, the solid support comprises microspheres or beads. "Microspheres," "beads," "particles," or grammatical equivalents herein are intended to mean small discrete particles made of various material including, but are not limited to, plastics, ceramics, glass, and polystyrene. In certain embodiments, the microspheres are magnetic microspheres or beads. Alternatively or additionally, the beads may be porous. The bead sizes range from nanometers, e.g. 100 nm, to millimeters, e.g. 1 mm.

Methods for Preparing a Library of Tagged Nucleic Acid Fragments

The present disclosure relates generally to methods for preparing a library of nucleic acid fragments, and more specifically to methods for preparing a library of nucleic acid fragments in a single reaction mixture, e.g., a single reaction tube or other container, using proteases, for a variety of applications including, e.g., next generation DNA sequencing, analysis of copy number variations, and analysis of single nucleotide variations.

There are a variety of methods and applications for which it is desirable to prepare a library of nucleic acid fragments from a minimal population of cells, e.g., a single cell, for various applications such as sequencing a genome. Current methods for preparing a library of nucleic acid fragments require a separate nucleic acid extraction and/or amplification step prior to DNA fragmentation. Typically, the cells are processed first to generate a cell lysate from which target nucleic acid content is extracted and purified. Then in a separate step, the purified target nucleic acid is subjected to fragmentation, e.g., using Nextera transposome available from Illumina, Inc (San Diego, Calif.). This separate nucleic acid extraction step and transfer of samples between reaction tubes or containers are usually wasteful of target nucleic acid sample, and thus render the nucleic acid fragments prepared less likely to sufficiently represent across the target nucleic acid from the sample. This insufficient representation becomes particularly challenging when the amount of cell sample is limited or difficult to obtain. Some methods have been developed to solve this problem in the case of a single or few cell input by a pre-amplification step. However, these methods do not efficiently solve the problem of insufficient representation and typically introduce high noises. The present disclosure provides a solution to this problem by using a single-reaction mixture, e.g., in a single tube, with add-on protocol to generate a library of nucleic acid fragments. The method provided herein integrates various steps, including generating cell lysate, tagmentation, and the like, in a single reaction tube, optionally using one or more add-on protocols. In such a single-tube add-on method, the amount of starting nucleic acid materials from the cells are preserved, and the library generated therefrom can thus better represent the target nucleic acid, e.g., a genome.

In one aspect, the present disclosure provides a method of preparing a library of tagged nucleic acid fragments including (a) contacting a population of cells directly with a lysis reagent to generate a cell lysate, wherein the lysis reagent has one or more proteases, and wherein the cell lysate contains a target nucleic acid; (b) inactivating the one or more proteases to form an inactivated cell lysate, and (c) directly applying at least one transposase and at least one transposon end composition containing a transferred strand to the inactivated cell lysate under conditions where the target nucleic acid and the transposon end composition undergo a transposition reaction to generate a mixture, wherein: (i) the target nucleic acid is fragmented to generate a plurality of target nucleic acid fragments, and (ii) the transferred strand of the transposon end composition is joined to 5' ends of each of a plurality of the target nucleic acid fragments to generate a plurality of 5' tagged target nucleic acid fragments.

In some embodiments, the cell sample is directly contacted with a combined lysis reagent containing one or more proteases and thus the proteases provided herein can directly contact with the intact cells. In some embodiments, the cell sample is contacted with a first lysis reagent containing detergents to generate a first cell lysate, and then a second lysis reagent containing one or more proteases is added to the reaction tube containing the first cell lysate. In this alternative, the proteases provided herein contact with the cell lysate. Example 1 provided below illustrates a method of generating a cell lysate containing target nucleic acid.

Exemplary lysis master mixture containing detergent and QIAGEN (San Diego, Calif.) protease (Part No. 19155) is illustrated in Example 1 and Tables 1-3.

The starting material according the method provided herein can be a minimal population of cells, with which the traditional sequencing protocols typically can only produce noisy sequencing data and copy number variation data due to insufficient representatives across target nucleic acid, e.g., a genome. In some embodiments, a minimal population of cells can contain one, two, three, four, or five cells. In some embodiments, a minimal population of cells can be less than 10 cells, less than 15 cells, less than 20 cells, less than 25 cells, less than 30 cells, less than 35 cells, less than 40 cells, less than 45 cells, less than 50 cells, less than 60 cells, less than 70 cells, less than 80 less, less than 90 cells, or less than 100 cells. In one embodiment, the starting material used in the present method contains only a single cell. In some embodiments, the target nucleic acid is genomic DNA. In some embodiments, the target nucleic acid contains chromosomal DNA or a fragment thereof. In some embodiments, the target nucleic acid comprises a genome or a partial genome.

The proteases used herein can digest chromatin proteins, e.g., histones, and other DNA binding proteins to release naked genomic DNA. In addition, the proteases provided herein can digest endogenous DNase to protect the genome from degradation. In some embodiments, the method herein uses only one protease possessing a broad specificity, and thus the proteases can digest various different proteins and polypeptides including some or many of the proteins in a cell. In some other embodiments, the broad specificity can be achieved by using a mixture of various proteases, and the combination of various proteases can digest various different proteins and polypeptides including some or many of the proteins in a cell. Exemplary proteases includes subtilisins such as ALCALASE, subtilisin carlsberg, subtilisin S41, heat-labile proteinase K, and Qiagen protease. Example 4 illustrates that protease activity is useful for uniform access to genomic DNA. It should be appreciated that different protease and/or mixture of proteases can be used depending on various conditions, e.g., cell type and sample amount.

The amount and concentration of proteases used in each reaction provided herein can vary depending on the amount of chromosome DNA and/or the number of the cells used as well as the activity of the proteases. In some embodiments, the concentration of one or more proteases in the cell lysate is 0.1 mg/ml to 10 mg/ml. In some embodiment, the concentration of one or more proteases in the cell lysate is 0.1 mg/ml to 2.5 mg/ml. In some embodiments, the concentration of one or more proteases in the cell lysate is 2 mAU/ml to 500 mAU/ml. In some embodiments, the concentration of one or more proteases in the cell lysate is 4.5 mAU/ml to 500 mAU/ml. In some embodiments, the concentration of one or more proteases in the cell lysate is 10 mAU/ml to 100 mAU/ml. The present disclosure exemplifies the testing and optimizing of the protease concentration using a protease, e.g., QIAGEN protease (Part No. 19155) as shown in Example 5. As shown in this example, when a single cell is treated with 0.5 mg/ml (equivalent to 22.5 mAU/ml) or 2 mg/ml (equivalent to 90 mAU/ml) protease under normal reaction temperature (e.g., room temperature), clean copy number analysis result is similarly achieved as shown in the top two histograms of FIG. 3A. Thus, in some embodiments, the concentration of the proteases in the cell lysate is 0.5 mg/ml to 2 mg/ml. Exemplary the concentrations of the proteases in the cell lysate include 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, and 2.0 mg/ml. In some embodiments, the concentration of one or more proteases in the cell lysate is 20 mAU/ml to 90 mAU/ml. Exemplary concentrations of one or more proteases in the cell lysate include 20 mAU/ml, 30 mAU/ml, 40 mAU/ml, 50 mAU/ml, 60 mAU/ml, 70 mAU/ml, 80 mAU/ml, 90 mAU/ml.

Various conditions including PH value can affect both the digestion by proteases and actives of other enzymes in the reaction tube, and thus these conditions, e.g., pH value, can be optimized. Example 6 illustrates optimizing pH condition of protease digestion reaction balancing the protease activity and sequencing results. As shown, the QIAGEN protease activity is analyzed under different pH conditions, and the activity of protease increases as pH value increases with protease having lowest activity at pH 7.0 and highest activity at pH 10.0 among the range from pH 7.0 to pH 10.0. Then, percentage of unique mapped read and noise in copy number data are analyzed under various pH conditions too. As shown, when pH is 7, 8 or 9, about 70% clean unique mapped reads can be achieved. However, when pH is 10, less percentage of unique mapped reads can be achieved and the data variation increases significantly. Similarly, when pH is 7, 8 or 9, count differences between neighboring bins are relatively small (about 20%) with small variations; while count differences between neighboring bins are significantly increased with huge variation at pH 10.0. Thus, in some embodiments, the population of cells is contacted with the lysis reagent at pH7.0 to pH10.0. In some embodiments, the population of cells is contacted with the lysis reagent at pH7.0 to pH 9.0. Exemplary pH condition includes pH 7.0, pH 7.5, pH 8.0, pH 8.5, pH 9.0, and pH 9.5.

Because nucleic acid preparation and tagmentation steps are performed in the same reaction tube, it can be beneficial that the proteases according to the present method can be effectively inactivated without disturbing the next tagmentation step which typically requires double-stranded DNA. In some embodiments, the proteases can be inactivated by increasing temperature prior to the tagmentation step. High temperature can denature double-stranded DNA conformation. Thus, in some embodiments, the proteases provided herein can be inactivated at relatively low temperature without denaturing double-stranded DNA. Example 7 illustrates testing heat inactivation of a protease. As shown, the protease activity is tested in different temperature, and the protease activity progressively decreases as the temperature increases, and is completely inactivated at 70° C. Thus, in some embodiments, one or more proteases are inactivated by increasing temperature to 50° C.-80° C. In some embodiments, the one or more proteases are inactivated by increasing temperature to 70° C.

In some embodiments, the proteases provided herein can also be inactivated by adding proteases inhibitors to the reaction tube. The protease inhibitors provided herein do not interfere with the tagmentation and amplification step to be carried out in the same reaction tube later. Exemplary protease inhibitors include, for example, AEBSF, bestatin, E-64, pepstatin A, phosphoramidon, leupeptin, aprotinin, bestatin hydrochloride, leupeptin, phosphoramidon disodium salt, elastatinal, aprotinin, nafamostat mesylate, antipain, PMSF (phenylmethanesulfonylfluoride), PefaBloc, diisopropylfluorophosphate, and Streptomyces subtilisin inhibitor.

As discussed above, one or more detergents can also be added to cells. In some embodiments, the detergents are added to the cells together with the proteases. In other embodiments, the detergents are added to the cells first followed by adding proteases to the reaction tube. The function of detergent used herein includes disrupting cell membranes and releasing intracellular materials in a soluble form. In some embodiments, the detergent used herein does not interfere with down-stream enzymatic activities. Thus, in some embodiments, nonionic detergents are used. These detergents break protein-lipid and lipid-lipid associations, but not protein-protein interactions, and thus are less likely to interfere other down-stream enzymes. Typically, non-ionic detergents contain uncharged, hydrophilic headgroups. Typical non-ionic detergents are based on polyoxyethylene or a glycoside. Exemplary non-ionic detergents include Tween® 80, Tween® 20Tween, Triton® X-100, Triton® X-100-R, Triton® X-114, NP-40, Genapol® C-100, Genapol® X-100, Igepal® CA 630, Arlasolve® 200, Brij® 96/97Triton, Brij® 98, Brij® 58, Brij® 35Brij series, Pluronic® L64, Pluronic® P84, non-detergent sulfobetaines (NDSB 201), amphipols (PMAL-C8), CHAPS, octyl β-D-glucopyranoside, saponin, nonaethylene glycol monododecyl ether (C12E9, polidocenol), sodium dodecyl sulfate, N-laurylsarcosine, sodium deoxycholate, bile salts, hexadecyltrimethyl ammonium bromide, SB3-10, SB3-12, amidosulfobetaine-14, octyl thioglucoside, maltosides, HEGA and MEGA series.

Once the proteases are inactivated, an in vitro transposition reaction can be carried out in the same reaction mixture, e.g., in the same reaction tube, by adding transposome composition containing a stable complex formed between the transposase and the transposon end composition or using separate transposase and transposon end composition. The in vitro transposition reaction catalyzed by a transposase results in simultaneously breaking a target nucleic acid into fragments and joining a tag to the 5' end of each fragment. It should be understood that any method that describes the use of a transposase and a transposon end composition could also use a transposome composition made from the transposase and the transposon end composition, and any method that describes the use of a transposome composition could also use the separate transposase and a transposon end composition of which the transposome composition is composed.

In some embodiments, the method provided herein includes incubating the inactivated cell lysate containing the target nucleic acid in an in vitro transposition reaction with at least one transposase and a transposon end composition with which the transposase forms a transposition complex, the transposon end composition including (i) a transferred strand that exhibits a transferred transposon end sequence and, optionally, an additional sequence 5'-of the transferred transposon end sequence, and (ii) a non-transferred strand that exhibits a sequence that is complementary to the transferred transposon end sequence, under conditions and for sufficient time wherein multiple insertions into the target nucleic acid occur, each of which results in joining of a first tag containing the transferred strand to the 5' end of a nucleotide in the target nucleic acid, thereby fragmenting the target nucleic acid and generating a population of annealed 5'-tagged DNA fragments, each of which has the first tag on the 5'-end of the target nucleic acid fragments.

In some embodiments, the method described above is performed using separate transposase and transposon end compositions. In other embodiments, the method described above is performed using a transposome composition comprising the complex formed between the transposase and the transposon end composition.

In some specific embodiments, the method provided herein is performed using Nextera Transposome available from the Illumina Inc (San Diego, Calif.), as described generally in the disclosure of US 2010/0120098, the content of which is incorporated herein by reference in its entirety.

Transposases and transposome compositions are generally known to those of skill in the art, as exemplified by the disclosure of US 2010/0120098, the content of which is incorporated herein by reference in its entirety. In some embodiments, the method provided herein employs a transposome composition formed by a hyperactive Tn5 transposase and a Tn5-type transposon end (Goryshin and Reznikoff, 1998, J. Biol. Chem., 273: 7367). In some embodiments, the method provided herein employs a transposome composition formed or by a MuA transposase and a Mu transposon end comprising R1 and R2 end sequences (Mizuuchi, 1983, Cell, 35: 785; Savilahti et al., 1995, EMBO J., 14: 4893). Any transposition system that is capable of inserting a transposon end in a random or in an almost random manner with sufficient efficiency to 5'-tag and fragment a target nucleic acid for its intended purpose can be used in the present disclosure. Exemplary transposome composition systems include but are not limited to Staphylococcus aureus Tn552 (Colegio et al., 2001, J Bacterid., 183: 2384-8; Kirby et al., 2002, Mol Microbiol, 43: 173-86), Ty1 (Devine and Boeke, 1994, Nucleic Acids Res., 22: 3765-72 and International Patent Application No. WO 95/23875), Transposon Tn7 (Craig, 1996, Science. 271: 1512; Craig, 1996, Review in: Curr Top Microbiol Immunol, 204: 27-48), TnlO and IS10 (Kleckner et al., 1996, Curr Top Microbiol Immunol, 204: 49-82), Mariner transposase (Lampe et al., 1996, EMBO J., 15: 5470-9), Tci (Plasterk, 1996, Curr Top Microbiol Immunol, 204: 125-43), P Element (Gloor, 2004, Methods Mol Biol, 260: 97-114), TnJ (Ichikawa and Ohtsubo, 1990, J Biol Chem. 265: 18829-32), bacterial insertion sequences (Ohtsubo and Sekine, 1996, Curr. Top. Microbiol. Immunol. 204:1-26), retroviruses (Brown et al., 1989, Proc Natl Acad Sci USA, 86: 2525-9), and retrotransposon of yeast (Boeke and Corces, 1989, Annu Rev Microbiol. 43: 403-34).

As non-limiting examples, transposon ends can include the 19-bp outer end ("OE") transposon end, inner end ("IE") transposon end, or "mosaic end" ("ME") transposon end recognized by a wild-type or mutant Tn5 transposase, or the R1 and R2 transposon end as set forth in the disclosure of US 2010/0120098, the content of which is incorporated herein by reference in its entirety. Transposon ends can include any nucleic acid or nucleic acid analogue suitable for forming a functional complex with the transposase or integrase enzyme in an in vitro transposition reaction. For example, the transposon end can include DNA, RNA, modified bases, non-natural bases, modified backbone, and can include nicks in one or both strands.

In some embodiments, wherein the transferred strand includes a 3'-portion and a 5'-portion, wherein the 3'-portion exhibits transferred transposon end sequence, and the 5'-portion of the transferred strand exhibits a sequence comprising one or more tag domains for a particular purpose (e.g., a sequencing tag domain or an amplification tag domain, and optionally an address tag domain for next-generation sequencing or amplification). Exemplary tag domains include a restriction site tag domain, a capture tag domain, a sequencing tag domain, an amplification tag domain, a detection tag domain, an address tag domain, and a transcription promoter domain.

In some embodiments, two different transposomes are used in the in vitro transposition reaction, and each of the two transposomes contains the same transposase but a different transposon end composition. In some embodiments, two different transposomes are used, and the two different transposomes each contains the same transposase and the transposon end compositions contain different transferred strands. In some embodiments, two different transposomes are used, and each of the two transposomes includes different transposase enzymes and different transposon end compositions, each of which forms a functional complex with the respective transposase.

In some embodiments, the amount of the transposase and the transposon end composition or of the transposome composition used in the in vitro transposition reaction is between about 1 picomole and about 25 picomoles per 50 nanograms of target nucleic acid per 50-microliter reaction. In some embodiments, the amount of the transposase and the transposon end composition or of the transposome composition used in the in vitro transposition reaction is between about 5 picomoles and about 50 picomoles per 50 nanograms of target nucleic acid per 50-microliter reaction. In some embodiments, concentration of the transposase is 0.5-1 nM. In some embodiments, concentration of the transposase is 0.01-0.02 picomoles per 20 µl reaction.

Example 2 illustrates a protocol for tagmentation step using a method provided herein. In the embodiments wherein a single-cell is used to prepare a library for sequencing, only two copies of genome are present, and thus smaller insert size tends to increase library diversity. As shown in Example 8, the counts, and thus the diversity represented by a library, increase as the insert size decreases. Therefore, in some embodiments, the method herein use higher amount of transposase in the tagmentation step to increase fragmentation and reduce insert size of the tagged nucleic acid fragments. As shown, when 1 µl Tn5 is used in a tagmentation reaction, the average fragment size is about 550 bp; while when 2 µl Tn5 is used in a tagmentation reaction, the average fragment size is about 400 bp. Consistent with smaller insert size, library diversity increases when treated with 2 µl Tn5 compared with that treated with 1 µl Tn5. Tn5 is used to illustrate adjustment of transposase. It should be appreciated that other transposases can also be used in the present methods and their amount can be adjusted and optimized using the method provided herein and methods known by those skilled in the art.

In some embodiments, the reaction time for the in vitro transposition reaction is two hours or less, one hour or less, 30 minutes or less, 15 minutes or less, or 10 minutes or less. In some embodiments, the reaction time for the in vitro transposition reaction is 5 minutes or less.

In some embodiments, the reaction temperature for the in vitro transposition reaction is from about 40° C. to about 70° C., from about 45° C. to about 65° C., or from about 50° C. to about 60° C. In some embodiments, the reaction temperature for the in vitro transposition reaction is about 55° C.

In some embodiments, the in vitro transposition reaction can be terminated by holding the sample, e.g., in a tube, at 4° C. In some embodiments, neutralize tagment buffer to the tagmentation products and incubate the sample at room temperature for 5 minutes.

Through an in vitro transposition reaction, target nucleic acid fragments are tagged at the 5' end. In some embodiments, the method provided herein further includes steps to incorporate a 3' end tag to the 5' tagged nucleic acid fragments to make a library of di-tagged nucleic acid fragments. In some embodiments, a library of di-tagged nucleic acid fragments is generated from 5' tagged target nucleic acid in a single tube without performing any intervening purification steps. Adding 3' end tag can be performed through various methods, e.g., by using DNA polymerase, terminal transferase, and/or ligase as described in WO 2010/048605 the content of which is incorporated by its entirety.

Thus, in some embodiments, the method provided herein further comprises (d) incubating the mixture from step (c) directly with at least one nucleic acid modifying enzyme under conditions wherein a 3' tag is joined to the 5' tagged target nucleic acid fragments to generate a plurality of di-tagged target nucleic acid fragments. In some embodiments, steps (a), (b), (c), and (d) are performed in a single reaction tube. Embodiments illustrating generation of a library of di-tagged nucleic acid fragments are discussed below.

In some embodiments, di-tagged nucleic acid fragments are generated by using a polymerase, e.g., a DNA polymerase, with strand-displacement or 5' nuclease activity. In some embodiments, the method provided herein includes incubating the population of annealed 5'-tagged nucleic acid fragments with a DNA polymerase that has strand-displacement or 5' nuclease activity under conditions without thermocycling and wherein the annealed 5'-tagged nucleic acid fragments are not denatured, wherein the DNA polymerase extends the 3'-end of each strand of the annealed 5'-tagged nucleic acid fragments using the complementary strand as a template and displaces or digests the non-transferred strand, thereby generating the library of di-tagged double-stranded DNA fragments. In one embodiment, the extension step was performed at 72° C. using the 5' tag on the opposite strand as a template.

In some embodiments, the di-tagged double stranded DNA fragments generated by the method provided above are denatured to generate a library of tagged DNA fragments containing di-tagged single stranded DNA fragments (e.g., by heating to 95° C. and rapidly cooling).

In other embodiments, di-tagged nucleic acid fragments are generated by using terminal transferase. In some embodiments, the 5'-tagged double stranded nucleic acid fragments are denatured to generate the 5'-tagged single stranded nucleic acid fragments. The 5'-tagged single stranded nucleic acid fragments are incubated with a DNA polymerase consisting of a terminal transferase and at least one substrate for the terminal transferase during which the terminal transferase joins a second tag to the 3' end of the 5'-tagged nucleic acid fragments, thereby generating a library of tagged nucleic acid fragments containing di-tagged nucleic acid fragments. In some embodiments, the 3'-end of the non-transferred transposon end that composes the transposon end composition is blocked (e.g., by using a non-transferred transposon end that has a dideoxy nucleotide or a 3'-O-methyl-nucleotide as the 3'-terminal nucleotide), which blocks 3' nucleotide and prevents addition by terminal transferase, thereby preventing background tagging of the non-transferred transposon end.

In other embodiments, the 5'-tagged double stranded nucleic acid fragments are not denatured to generate the 5'-tagged single stranded nucleic acid fragments. Instead, the 5'-tagged nucleic acid fragments are incubated, without a prior denaturation step, with a DNA polymerase consisting of a terminal transferase and at least one substrate for the terminal transferase under conditions and for sufficient time wherein the terminal transferase joins the second tag to the 3' end of the 5'-tagged nucleic acid fragments, thereby generating a library of di-tagged nucleic acid fragments. In some embodiments, the 3'-end of the non-transferred transposon end that composes the transposon end composition is blocked (e.g., by using a non-transferred transposon end that has a dideoxy nucleotide or a 3'-O-methyl-nucleotide as the 3'-terminal nucleotide).

In other embodiments, di-tagged nucleic acid fragments are generated by using a DNA polymerase and a terminal tagging oligonucleotide. In some embodiments, the 5'-tagged double stranded nucleic acid fragments are denatured to generate 5'-tagged single stranded nucleic acid fragments (e.g., by heating to 95° C. and rapidly cooling), and a second tag is joined to the 3' end of 5'-tagged single stranded nucleic acid fragment using a DNA polymerase and a terminal tagging oligonucleotide, thereby generating a library of di-tagged nucleic acid fragments. In some embodiments, steps of joining the second tag to the 3' end of the 5'-tagged nucleic acid fragments using a DNA polymerase and a terminal tagging oligonucleotide includes: (1) providing a terminal tagging oligonucleotide having a 5'-portion and 3'-portion, the 5'-portion exhibits a sequence that is complementary to the sequence of the second tag that it is desired to join to the 3'-termini of the 5'-tagged single stranded nucleic acid fragments, and the 3'-portion exhibits a random sequence containing between three and eight random nucleotides, of which, the 3'-terminal nucleotide is blocked so that it is not capable of being extended by the DNA polymerase; (2) contacting the 5'-tagged single stranded nucleic acid fragments with the terminal tagging oligonucleotide under conditions and for sufficient time wherein the terminal tagging oligonucleotide anneals to the 5'-tagged single stranded nucleic acid fragments; and (3) contacting the 5'-tagged single stranded nucleic acid fragments to which the terminal tagging oligonucleotide is annealed with the DNA polymerase in a reaction mixture and under DNA polymerization conditions and for sufficient time wherein the 3'-termini of the 5'-tagged single stranded nucleic acid fragments are extended using the terminal tagging oligonucleotide as a template, whereby the second tag is joined to their 3'-termini and 5'- and 3'-tagged single stranded nucleic acid fragments are generated.

In yet other embodiments, di-tagged nucleic acid fragments are generated by using a template-dependent ligase and a ligation tagging oligonucleotide. In some embodiments, the 5'-tagged nucleic acid fragments are incubated with a template-dependent DNA ligase and a ligation tagging oligodeoxynucleotide having a 3'-portion and a 5'-portion, wherein the 3'-portion exhibits a second tag that exhibits any sequence that is desired to be joined to the 3'-end of the 5'-tagged DNA fragments and the 5'-portion has a 5'-monophosphate group and exhibits a random sequence, under conditions and for sufficient time wherein the second tag is joined to the annealed 5'-tagged DNA fragments, thereby generating a library of DNA fragments comprising annealed di-tagged DNA fragments. In some embodiments, the method further includes the step of denaturing the library of DNA fragments comprising annealed di-tagged DNA fragments (e.g., by heating to 95° C. and rapidly cooling), thereby generating a library of di-tagged single stranded DNA fragments.

After a library of tagged nucleic acid fragments is generated, the tagged nucleic acid fragments can be amplified, e.g., using limited-cycle polymerase chain reaction (PCR), to introduce other end sequences or adaptors, e.g., index, universal primers and other sequences required for cluster formation and sequencing. In some embodiments, such amplification is performed to a library of 5' tagged nucleic acid fragments. In some embodiments, such amplification is performed to a library of di-tagged nucleic acid fragments. In some embodiments, the amplification is performed in the same reaction tube where the library of tagged nucleic acid fragments is generated, and the agents for amplification are directly added to the same reaction tube.

Thus, the method provided herein further includes (e) amplifying one or more di-tagged target nucleic acid fragments to generate a library of tagged nucleic acid fragments with additional sequence at 5' end and/or 3' end of the di-tagged nucleic acid fragments. In some embodiments, steps (a), (b), (c), (d), and (e) are performed in a single reaction tube. Exemplary amplification methods include polymerase chain reaction (PCR), strand-displacement amplification reaction, rolling circle amplification reaction, ligase chain reaction, transcription-mediated amplification reaction, and loop-mediated amplification reaction.

In some embodiments, the method provided herein includes amplifying the library of di-tagged single stranded nucleic acid fragments using a PCR. In some embodiments, the method provided herein uses single-primer PCR amplification of a library of di-tagged DNA fragments. In some embodiments, the step of amplifying di-tagged DNA fragments includes using a DNA polymerase and at least one primer that is complementary to the second tag. In some embodiments, the step of amplifying the library of di-tagged DNA fragments includes amplifying the library of tagged DNA fragments by PCR using only one oligodeoxyribonucleotide that exhibits the sequence of at least a portion of the transferred strand as a PCR primer and the di-tagged DNA fragments as templates. In some embodiments, the primer contains a 5' portion that contains additional sequence, e.g., an adaptor sequence.

In some embodiments, two different PCR primers are used, each of which PCR primers exhibits the sequence of at least a portion of the transferred transposon end that composes the transposon end composition. In some embodiments, each PCR primer includes a 3'-portion and a 5'-portion, wherein the 3'-portion exhibits the respective transferred transposon end sequence and the 5'-portion exhibits the sequence of a respective tag domain or an adaptor for a particular purpose (e.g., a sequencing tag domain/adaptor or an amplification tag domain/adaptor, and optionally an address tag domain/adaptor for next-generation sequencing or amplification). For example, when a single transposon end composition is used in the in vitro transposition reaction to generate the library of di-tagged DNA fragments using a DNA polymerase that has strand-displacement or 5' nuclease activity, the di-tagged DNA fragments can be amplified by PCR using two different PCR primers. Each PCR primer contains a 3'-portion and a 5'-portion, wherein the 3'-portion exhibits the respective transferred transposon end sequence and the 5'-portion exhibits the sequence of a respective tag domain/adaptor for a particular purpose (e.g., a sequencing tag domain/adaptor or an amplification tag domain/adaptor, and optionally an address tag domain/adaptor for next-generation sequencing or amplification). In some embodiments, the 5' portion of each PCR primer is different from that of the other primer, and as such the sequences of the two ends of the PCR product are different. For example, one end contains one index and/or universal primer sequence, and the other end contains a different index and/or universal primer sequence.

In some embodiments, the two ends of di-tagged nucleic acid fragments originate from two different transferred strand sequences. For example, in some embodiments, two different transposomes can be used in the in vitro transposition reaction, and each of the two transposomes contains the same transposase but a different transposon end composition. In some embodiments, two different transposomes are used, and the two different transposomes each contains the same transposase and the transposon end compositions contain different transferred strands. In some embodiments, two different transposomes are used, and each of the two transposomes includes different transposase enzymes and different transposon end compositions, each of which forms a functional complex with the respective transposase. In some embodiments, wherein two different transposon end compositions are used in the in vitro transposition reaction, and the library of di-tagged single stranded nucleic acid fragments is generated using a DNA polymerase that has strand-displacement or 5' nuclease activity, the first tag exhibits the sequence of the transferred strand of one transposon end composition and the second tag exhibits the sequence of the non-transferred strand of the other transposon end composition.

In the above mentioned embodiments and other embodiments wherein two different transferred strands are linked to the 5' end of each opposite strands of the double stranded nucleic acid, the method provided herein can further include the step of amplifying the di-tagged nucleic acid fragments by PCR using two different PCR primers. One of the PCR primers exhibits the sequence of at least a portion of one transferred strand that compose one transposon end composition, and the other of PCR primers exhibits the sequence of at least a portion of the other transferred strand that composes the other transposon end composition.

In some embodiments wherein two primers are used, each PCR primer contains a 3'-portion and a 5'-portion, wherein the 3'-portion exhibits the respective transferred transposon end sequence and the 5'-portion exhibits the sequence of a respective tag domain/adaptor for a particular purpose (e.g., a sequencing tag domain or an amplification tag domain, and optionally an address tag domain for next-generation sequencing or amplification). In some embodiments, the 5' portion of each PCR primer is different from that of the other primer, and as such to introduce different sequences to the two ends of the PCR product. In some embodiments, the 5' portion of the first PCR primer or the 5' portion of the second PCR primer, or the 5' portions of both the first and the second PCR primers contain first or second sequencing tags/adaptors, respectively, for generation of templates for next-generation sequencing for a particular sequencing platform (e.g., sequencing tags for an Illumina Nextera sequencing platform). In some embodiments, the 5' portion of the first PCR primer or the 5' portion of the second PCR primer additionally contains an address tag domain/adaptor or another tag domain/adaptor for a particular purpose.

Example 3 illustrates a limited-cycle PCR amplification that can add other sequences at the two ends of the tagged nucleic acid fragments, e.g., index 1 (i7) and index 2 (i5) (from Illumina, Inc, San Diego, Calif.) and sequences required for other purposes, e.g., cluster formation. In a single-cell sequencing, the input DNA is relative small, and thus the cycle number of PCR can be adjusted to achieve better sequencing results. In Example 9, the cycle number of PCR is tested and optimized using a single cell as starting material. As shown, the noise is big when PCR with 16 cycles is used in a copy number analysis, and the noise is significantly reduced when PCR with 18 cycles or 20 cycles is used. Thus, in some embodiments, the number of PCR cycle is 18, 19 or 20.

A wide variety of enzymes and kits are available for performing the amplification reaction by PCR as known by those skilled in the art. For example, in some embodiments, the PCR amplification is performed using either the FAIL-SAFE™ PCR System or the MASTERAMP™ Extra-Long PCR System from EPICENTRE Biotechnologies, Madison, Wis., as described by the manufacturer. However, the present disclosure is not limited to the use of those products or conditions for the amplification reaction and any suitable thermostable DNA polymerase and reaction mixture that permits amplification of the sequence between the primer that anneals to the target sequence and the primer that anneals to the transposon can be used.

The method provide herein is not limited to the use of PCR to amplify the library of tagged nucleic acid fragments. Any suitable amplification method (e.g., rolling circle amplification, riboprimer amplification (e.g., U.S. Pat. No. 7,413,857), ICAN, UCAN, ribospia, terminal tagging (U.S. Patent Application No. 20050153333), Eberwine-type aRNA amplification or strand-displacement amplification) that amplifies the same sequence, and generates a suitable composition and amount of amplification product for the intended purpose can be used in embodiments of the present invention. For example, some strand displacement methods that can be used are described in PCT Patent Publication Nos. WO 02/16639; WO 00/56877; and AU 00/29742; of Takara Shuzo Company, Kyoto, Japan; U.S. Pat. Nos. 5,523, 204; 5,536,649; 5,624,825; 5,631,147; 5,648,211; 5,733, 752; 5,744,311; 5,756,702; and 5,916,779 of Becton Dickinson and Company; U.S. Pat. Nos. 6,238,868; 6,309,833; and 6,326,173 of Nanogen/Becton Dickinson Partnership; U.S. Pat. Nos. 5,849,547; 5,874,260; and 6,218,151 of Bio Merieux; U.S. Pat. Nos. 5,786,183; 6,087,133; and 6,214, 587 of Gen-Probe, Inc.; U.S. Pat. No. 6,063,604 of Wick et al; U.S. Pat. No. 6,251,639 of Kurn; U.S. Pat. No. 6,410,278; and PCT Publication No. WO 00/28082 of Eiken Kagaku Kabushiki Kaishi, Tokyo, Japan; U.S. Pat. Nos. 5,591,609; 5,614,389; 5,773,733; 5,834,202; and 6,448,017 of Auerbach; and U.S. Pat. Nos. 6,124,120; and 6,280,949 of Lizardi.

In some embodiments, the libraries of tagged nucleic acid fragments prepared by any method of the present disclosure can then be subject to steps for purifying the library nucleic acid and optionally for providing a size selection. These steps can help clean up the PCR products and remove nucleic acid with undesirable size. Various methods in the art can be used to clean nucleic acid fragments generated in the present methods, including but not limited to, using columns to clean up the fragments, e.g., using QIAGEN QIAQUICK PCR purification kit, and using gel size selection, e.g., using Pippin Prep electrophoresis platform. Other methods for cleaning up nucleic acid fragments and/or for selecting nucleic acid size known in the art can also be used in the method provided herein.

For example, in some embodiments, AMPURE XP beads (from Beckman Coulter Genomics) are used to purify the tagged nucleic acid fragments. Nucleic acid fragments can bind to solid-phase reversible immobilization (SPRI) beads, and the affinity of the nucleic acid fragments with different length to the beads can be controlled by altering the PEG/NaCl concentration. Thus, by altering the PEG/NaCl concentration, nucleic acid with different size can be selectively purified. In some embodiments, the method provided herein uses a single AMPURE XP treatment to remove nucleic acid fragments below a certain size (e.g., 150-200 bp). In some embodiments, a double (upper and lower) size selection can be performed by two consecutive AMPURE XP steps. In the first selection step, a low concentration of AMPURE XP beads is added to the sample to bind larger DNA fragments. In this step the beads containing the larger fragments are discarded. Then in the second selection step, more beads are then added to the supernatant. In this second step, the amount of PEG and NaCl is increased so that smaller fragment sizes will be bound. Next the supernatant containing very short library fragments is discarded and the beads are washed and intermediate fragments are eluted. Those skilled in the art would understand that depending on the concentrations of PEG and NaCl in the first and final SPRI step distinct size ranges can be generated as illustrated in Bronner et al., 2009, Curr Protoc Hum Genet. 18:10.

Typical procedure for cleaning up a library of nucleic acid fragments using AMPURE XP beads includes (1) vortexing AMPURE XP beads to ensure that the beads are evenly dispersed; (2) adding certain amount of AMPURE XP beads to each PCR product generated and incubating at room temperature; (3) placing the tubes in a tube holder on the magnetic stand until the supernatant has cleared; (5) removing and discarding the supernatant; (6) without removing the tubes from the magnetic stand, washing the beads once or multiple times; (7) with the tubes still on the magnetic stand, allowing the beads to air-dry; (8) removing the tubes from the magnetic stand and adding resuspension buffer and incubating at room temperature; and (9) transferring the supernatant to fresh tubes.

After the library of nucleic acid fragments are cleaned up and size selected, it can be further subject to a library normalization step to normalize the quantity of each library and ensure that roughly equal library representation in each pooled sample. In some embodiments, a bead-based library normalization process is used in the method provided herein. In a bead-based library normalization process, roughly equal amount of beads are added to each well containing a sample of nucleic acid fragments. Because the amount of the beads added in each well are roughly equal, the amount of nucleic acid fragments attached to the beads are also roughly equal in each well. As such, after the supernatant is removed, and nucleic acid fragments eluted from the beads can be in roughly equal amount in each well.

A typical bead-based library normalization process includes (1) adding roughly equal amount of beads (e.g., in a bead buffer) into each well containing nucleic acid fragments generated in the methods provided above; (2) incubating and/or shaking to allow binding of the beads with nucleic acid fragments; (3) placing wells (can be on a plate) on a magnetic stand and allowing the supernatant to become cleared; (4) with wells on the magnetic stand, carefully removing and discarding the supernatant; (5) washing beads once or multiple times; and (6) eluting the nucleic acid fragments attached to the beads.

In some embodiments, the library of tagged nucleic acid fragments generated by the method provided herein can be used as templates for nucleic acid sequencing.

In some embodiments, prior to sequencing, the tagged nucleic acid fragments in the library are amplified to intensify signals against noise during a sequencing, e.g., in a sequencing by synthesis. In some embodiments, the library of tagged nucleic acid fragments is used as template for an amplification reaction (e.g., a PCR amplification reaction using PCR primers that are complementary to end sequences of the tagged nucleic acid fragments). In some embodiments, the library of amplified tagged nucleic acid fragments contains most or approximately all of the sequences exhibited by the target nucleic acid. In some embodiments wherein the target nucleic acid includes genomic DNA of an organism, the amplification reaction is a whole genome amplification reaction.

In some embodiments, the tagged nucleic acid fragments can be immobilized on a solid surface. For example, the solid surface can be attached with a polynucleotide complementary to an end sequence of tagged nucleic acid fragments, and as such the tagged nucleic acid fragments can be immobilized on the solid surface. Then the immobilized nucleic acid fragments are amplified on the surface. For example, in some embodiments, the immobilized nucleic acid fragments are amplified using cluster amplification methodologies as exemplified by the disclosures of U.S. Pat. Nos. 7,985,565 and 7,115,400, the contents of each of which is incorporated herein by reference in its entirety. The incorporated materials of U.S. Pat. Nos. 7,985,565 and 7,115,400 describe methods of solid-phase nucleic acid amplification which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays." The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, e.g., via a covalent attachment. Cluster amplification methodologies are examples of methods wherein an immobilized nucleic acid template is used to produce immobilized amplicons. Other suitable methodologies known in the art can also be used to produce immobilized amplicons from immobilized tagged nucleic acid fragments produced according to the methods provided herein.

The library of tagged nucleic acid fragments prepared according to the method provided herein can be sequenced according to any suitable sequencing methodology, such as direct sequencing, including sequencing by synthesis, sequencing by ligation, sequencing by hybridization, nanopore sequencing and the like. In some embodiments, the immobilized DNA fragments are sequenced on a solid support. In some embodiments, the solid support for sequencing is the same solid support upon which the amplification occurs.

In some embodiments, the sequencing methodology used in the method provided herein is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., 1996, *Analytical Biochemistry* 242 (1), 84-9; Ronaghi, 2001, *Genome Res.* 11(1), 3-11; Ronaghi et al., 1998, *Science* 281(5375), 363; U.S. Pat. Nos. 6,210, 891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons.

Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al., 2003, *Science* 299, 682-686; Lundquist et al., 2008, *Opt. Lett.* 33, 1026-1028; Korlach et al., 2008, *Proc. Natl. Acad. Sci. USA* 105, 1176-1181, the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Another useful sequencing technique is nanopore sequencing (see, for example, Deamer et al., 2000, *Trends Biotechnol.*, 18, 147-151; Deamer et al., 2002, *Acc. Chem. Res.* 35:817-825; Li et al., 2003, Nat. Mater. 2:611-615), the disclosures of which are incorporated herein by reference). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al., 2007, *Clin. Chem.*, 53, 1996-200; Healy, 2007, Nanomed. 2, 459-481; Cockroft et al., 2008, *J. Am. Chem. Soc.*, 130, 818-820, the disclosures of which are incorporated herein by reference).

In some embodiments, the method provided herein further includes analyzing copy number variation of a cell. A copy number analysis tests for DNA copy number variation in a sample. Such analysis helps detect chromosomal copy number variation that may cause or may increase risks of various critical disorders. For example, autism has been reported to be associated with copy number mutations (Sebat et al., 2007, Strong association of de novo copy number mutations with autism, *Science* 316 (5823): 445-9). It has also been reported that schizophrenia is associated with copy number varations (St Clair, 2008, Copy number variation and schizophrenia, *Schizophr Bull* 35 (1): 9-12). Various methods have been developed for detecting copy number variation. However, when starting material is limited and comes from a minimal population of cells, the noise is significant and result is compromised. The present method provides a method for detecting copy number variation in such situation. Examples provided below demonstrate copy number variation analysis using the present methods and several parameters are optimized for copy number variation analysis. In some embodiments, the minimal population of cells used in the copy number variation analysis contains one, two, three, four, or five cells. Typically, as cell number increases, more complete read distribution can be achieved and thus less noise is present in the data as shown in Example 10. In this example, the read distribution using one, three or five cells in analyzed in this example. As shown, genomic coverage increases as the cell number increases, it is estimated that one cell can cover about 40% of the genome, and three cells can cover more than 50% of genome, and five cells can cover about 60% of the genome. The average library counts using one cell, three cells, and five cells are about 5 million, 15 million, and 20 million, respectively. Also shown in this example, when a single cell is used, the overall success rate is relatively high 94% (N=187). One cell assay failures are likely caused by quality of the cell itself, e.g., selecting one of replicating cells or apoptotic/necrotic cells.

Example 11 compares the present method with some current single cell preparation methods. When the REPLI-g Single Cell Kit developed by QIAGEN (San Diego, Calif.) is used for preparation nucleic acid, the copy number variation data is very noisy when derived from a single cell, three cells or five cells. When SurePlex (PicoPlex) developed by Illumina, Inc (San Diego, Calif.) is used for preparing nucleic acid, it reduces noises compared with REPLI-g Single Cell Kit. As shown, the present method (Nextera SC) further reduces the noise compared with using SurePlex Amplification System. Thus, the present method provides an advanced method for analyzing copy number variation.

One aspect of copy number variation analysis is to detect mosaicism. A mosaic or mosaicism denotes the presence of two or more genotypes in one individual. There are two major types of mosaicism: somatic mosaicism and germline mosaicism. Somatic mosaicism occurs when the somatic cells contain more than one genotype, e.g., due to mitotic errors at first or later cleavages. Researchers have shown that somatic mutations are increasingly present throughout a lifetime and are responsible for many leukemia, lymphomas, and solid tumors (Jacobs et al., 2012, Detectable Clonal Mosaicism and Its Relationship to Aging and Cancer, *Nature Genetics* 44 (6): 651-U668). In germline mosaicism, some gametes (sperm or oocytes) carry a mutation, but the rest are normal, which also leads to many diseases. Thus, detection of mosaicism can provide valuable diagnostic information. The present disclosure provides methods for detecting mosaicism. In Example 12, using the method provided herein to detect mosaicism is exemplified. As shown, a population representing 15.4 MB DNA is detected in each single-cell sequencing in a copy number analysis of chromosome 18 of a single GM50121 cell. Similarly, copy number analysis data of chromosomes 15, X, and 10 using a single GM20916, and copy number analysis data of chromosomes 1 and 11 using a single GM10239 cell both detect additional populations representing other chromosomes.

The present methods can also be used for other applications, e.g., pre-implantation genetic screening, single cell research, analysis of circulating tumor cells, fine needle aspiration biopsy, buffy coat, and analysis of amniocytes. In these applications, the nucleic acid material to start with is usually limited, and thus the present method can improve analysis for these applications. Besides copy number variation analysis, the present method can also be used to detect single nucleotide variant present in a minimal population of cells in the above mentioned applications. Single nucleotide variant includes single nucleotide polymorphism (SNP) and point mutation. Single nucleotide polymorphism (SNP) is a common type of genetic variation which includes polymorphism in a DNA position at which two or more alternative bases occur at appreciable frequency in the people population (usually more than or equal to 1%). Point mutations are base variations with the frequency less than 1%. Single nucleotide polymorphism (SNP) and point mutations represent the largest source of diversity in the genome of a human. These single nucleotide polymorphisms (SNP) and point mutations can serve as biological markers for locating a disease on the human genome map because they are usually located near a gene associated with a certain disease. Thus, detection of single nucleotide polymorphisms (SNPs), point mutations, and similar mutations are of great importance to clinical activities, human health, and control of genetic disease. The present method provides advantage of uniform access to genomic DNA, and helps to preserve target nucleic acid material. Thus, it can improve single nucleotide variation detection using a minimal population of cells.

In the description of some embodiments of the various methods above, "reaction tube" or "tube" is used. It should be appreciated that other reaction mediums and/or containers can also be used in the present methods.

Kits for Preparing a Library of Tagged Nucleic Acid Fragments

In another aspect, the present disclosure provides a kit for preparing a library of tagged nucleic acid fragments comprising: (a) a lysis reagent having one or more proteases, and (b) a transposition reaction composition having at least one transposase and at least one transposon end composition containing a transferred strand.

In some embodiments, the lysis reagent provided includes only one protease possessing a broad specificity, and thus the proteases can digest various proteins and polypeptides. In some other embodiments, the lysis reagent provided herein includes a mixture of various proteases, and the combination of various proteases can digest various proteins and polypeptides. Exemplary proteases provided herein include serine proteases, threonine proteases, cysteine proteases, aspartate proteases, glutamic acid proteases, and metalloproteases. Exemplary protease used herein includes a serine protease isolated from a recombinant *Bacillus* strain. Exemplary proteases used herein include subtilisin and variants thereof, including subtilisin Carlsberg, ALCALASE, and subtilisin S41. Subtilisins and variants thereof are known to those of skill in the art and include, for example ALCALASE, ALCALASE 0.6L, ALCALASE 2.5L, ALK-enzyme, bacillopeptidase A, bacillopeptidase B, *Bacillus subtilis* alkaline proteinase bioprase, bioprase AL 15, bioprase APL 30, colistinase, subtilisin J, subtilisin S41, subtilisin Sendai, subtilisin GX, subtilisin E, subtilisin BL, GENENASE I, ESPERASE, MAXATASE, thermoase PC 10, protease XXVII, thermoase, SUPERASE, subtilisin Carlsberg subtilisin DY, subtilopeptidase, SP 266, SAVINASE 8.0L, SAVINASE 4.0T, KAZUSASE, protease VIII, OPTICLEAN, protin A 3L, SAVINASE, SAVINASE 16.0L, SAVINASE 32.0L EX, orientase 10B, protease S, serine endopeptidase. In particular embodiments of the methods and compositions presented herein, a heat-labile protease such as subtilisin and heat-labile variants of subtilisin can be used, as represented by the exemplary disclosure of Davail et al., 1994, *J. Biol. Chem.*, 26:17448-17453, which is incorporated herein by reference in its entirety.

In some embodiments, the lysis reagent includes one or more detergents. In some embodiments, the detergent provided herein does not interfere with down-stream enzymatic activities. Thus, in some embodiments, the lysis reagent includes nonionic detergents. Typically, non-ionic detergents contain uncharged, hydrophilic headgroups. Typical non-ionic detergents are based on polyoxyethylene or a glycoside. Exemplary non-ionic detergents include Tween® 80, Tween® 20Tween, Triton® X-100, Triton® X-100-R, Triton® X-114, NP-40, Genapol® C-100, Genapol® X-100, Igepal® CA 630, Arlasolve® 200, Brij® 96/97Triton, Brij® 98, Brij® 58, Brij® 35Brij series, Pluronic® L64, Pluronic® P84, non-detergent sulfobetaines (NDSB 201), amphipols (PMAL-C8), CHAPS, octyl β-D-glucopyranoside, saponin, nonaethylene glycol monododecyl ether (C12E9, polidocenol), sodium dodecyl sulfate, N-laurylsarcosine, sodium deoxycholate, bile salts, hexadec yltrimethyl ammonium bromide, SB3-10, SB3-12, amidosulfobetaine-14, octyl thioglucoside, maltosides, HEGA and MEGA series. In one embodiment, the lysis reagent includes components provided in Tables 1-3.

In some embodiments, the transposition composition contains at least one transposase and at least one transposon end composition including (i) a transferred strand that has a 3'-portion that exhibits the transferred transposon end sequence and a 5'-portion that exhibits the sequence for a tag domain for use in a next-generation sequencing or amplification reaction, and (ii) a 5'-phosphate-containing non-transferred strand that exhibits only the non-transferred transposon end sequence, wherein the transposase forms a complex with the transposon end composition that is active in an in vitro transposition reaction. In some embodiments, the kit further includes a reaction buffer that contains dimethylformamide in an amount that results in it being present in the in vitro transposition reaction at a final concentration of 10%. In some embodiments, the tag domain includes one or more of a restriction site domain, a capture tag domain, a sequencing tag domain, an amplification tag domain, a detection tag domain, and an address tag domain.

In some embodiments, the transposition reaction composition includes two or more transposon end compositions, each of the two or more transposon end compositions includes a transferred strand that differs by at least one nucleotide.

In some embodiments, the transposase is a Tn5 transposase. In some embodiments, the transposon end composition includes a Tn5 transposon end. In one embodiment of the kit, the transposome includes a wild-type or hyperactive Tn5 transposase or MuA transposase that is provided at a concentration wherein the final concentration of the transposome in the in vitro transposition reaction is at least 250 nM. In some other embodiments, the final concentrations of wild-type or hyperactive Tn5 transposome or MuA transposome is at least 500 nM.

In one embodiment, the transposase in the kit is a wild-type or mutant form of Tn5 transposase (e.g., EZ-Tn5™ transposase) at a concentration of greater than or equal to about 5 units per microliter; about 10-20 units per microliter; about 20-40 units per microliter; about 40-60 units per microliter; about 60-80 units per microliter; or about 80-100 units per microliter. In some embodiments, the kit provided herein includes components provided in Table 6.

In some embodiments, the kit additional includes a modifying enzyme. In some embodiments, the modifying enzyme is a polymerase or a ligase. In some embodiments, the kit includes at least one other enzyme component selected from among: a DNA polymerase that has 5' nuclease or strand-displacement activity; a DNA polymerase that lacks 5' nuclease activity, a template-dependent NAD ligase, and a template-independent ligase. In some embodiments, the at least one other enzyme component is selected from among: FAILSAFE™ DNA polymerase mix; Taq DNA polymerase, TfI DNA polymerase, T4 DNA polymerase, E. coli DNA ligase, bacteriophage TS2126 thermostable RNA ligase, Mth Rn 1 thermostable RNA ligase, and CIRCLIGASE™ thermostable ssDNA ligase.

In some embodiments wherein the at least one enzyme in the kit is a template-dependent ligase (e.g., E. coli DNA ligase), a high proportion of the ligase molecules are adenylated and ATP is not provided in the kit. In some embodiments wherein the at least one enzyme in the kit is a template-dependent ligase (e.g., E. coli DNA ligase), the kit additionally includes a ligation tagging oligonucleotide comprising a 3'-portion and a 5'-portion, wherein the 3'-portion exhibits a sequence of a tag domain and the 5'-portion exhibits a random sequence consisting of about three to about eight nucleotides. In some embodiments, the ligation tagging oligonucleotide includes a 5'-portion that exhibits a random sequence consisting of four nucleotides.

In some embodiments wherein the at least one enzyme in the kit is a template-independent ligase, selected from among bacteriophage TS2126 thermostable RNA ligase, Mth Rn 1 thermostable RNA ligase, and CIRCLIGASE™ thermostable ssDNA ligase, the template-independent ligase is provided in a highly adenylated form and ATP is not provided in the kit. In one embodiment of the kit includes EZ-Tn5™ transposase and the template-independent nucleic acid ligase, the EZ-Tn5 pMEDS transposon end composition includes both an EZ-Tn5 METS transferred strand that has a 5'-monophosphate group and an EZ-Tn5 pMENTS non-transferred strand that has a 5'-monophosphate group.

In some embodiments, the kit further includes a reagent for an amplification reaction. In some embodiments, the reagent for the amplification reaction is a reagent for PCR. In some embodiments, the reagent for the amplification reaction includes at least one primer. In some embodiments, the at least one primer includes a 3' portion that exhibits the sequence of at least a portion of the transferred strand. In some embodiments, the at least one primer includes a 5' portion that contains a universal sequence.

In some embodiments, the kit includes two primers, each PCR primer contains a 3'-portion and a 5'-portion, wherein the 3'-portion exhibits the respective transferred transposon end sequence and the 5'-portion exhibits the sequence of a respective tag domain/adaptor for a particular purpose (e.g., a sequencing tag domain or an amplification tag domain, and optionally an address tag domain for next-generation sequencing or amplification). In some embodiments, the 5' portion of each PCR primer is different from that of the other primer. In some embodiments, the 5' portion of the first PCR primer or the 5' portion of the second PCR primer, or the 5' portions of both the first and the second PCR primers contain first or second sequencing tags/adaptors, respectively. In one embodiment, the kit provided herein includes the components provided in Table 7.

In some embodiments, the kit further includes a size selection reagent. In some embodiments, the size selection reagent includes AMPURE XP beads (from Beckman Coulter Genomics). Nucleic acid fragments can bind to solid-phase reversible immobilization (SPRI) beads. In some embodiments, the size selection reagent further includes PEG and NaCl.

In some embodiments, the kit provided herein further includes a library normalization reagent. In some embodiments, the library normalization reagent includes Library Normalization Additives provided by Illumina, Inc (San Diego, Calif., Part No. 15025391) and Library Normalization Beads provided by Illumina, Inc (Part No. 15022566). In some embodiments, the library normalization reagent further includes Library Normalization Wash provided by Illumina, Inc (Part No. 15022565). In some embodiments, the library normalization reagent further includes library normalization storage buffer provided by Illumina, Inc (San Diego, Calif., Part No. 15025139).

In some embodiments, the kit further includes an apparatus having a solid surface. In some embodiments, the solid surface is attached with a population of oligonucleotides. In some embodiments, the apparatus is a flow cell apparatus. In some embodiments, the solid surface includes a patterned surface suitable for immobilization of molecules in an ordered pattern.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following examples are provided by way of illustration, not limitation.

EXAMPLES

Example 1 Generation of Cell Lysate Containing Target Nucleic Acid

In some embodiments, during the step of generating a cell lysate, cell membranes are disrupted by the detergent during which protein-lipid and lipid-lipid association are broken, and thereby releasing intracellular materials in soluble form. The major function of broad-specificity protease is to remove DNA-binding proteins such as histones from the DNA to allow uniform access of the transposase to the DNA. In some embodiments, as illustrated in this example, the detergent and the protease provide are in a single lysis reagent mixture. The mixture is directly applied to the cells for generating a cell lysate containing the target nucleic acid. As discussed above, in some embodiments, when heat is used to inactivate the protease, it is important that the heat does not denature the double-stranded nucleic acid, and to ensure that the tagmentation step is not interfered.

In this example, the protease can be heat inactivated at 70° C., and at this temperature the double stranded conformation of the DNA is preserved. A protocol for generation of a cell lysate containing target nucleic acid is illustrated in Example 1 as follows:

(1) Adequately mixed reagents by gently inverting and flicking the tubes 3-5 times, followed by a brief spin in a microcentrifuge.

(2) In a clean microcentrifuge tube, combine the components in Table 1 to make the 5× lysis master mixture. The lysis master mixture can be scaled up according to the number of samples, e.g., 10% extra to compensate for losses during pipetting can be included.

TABLE 1

Components of Lysis Mater Mixture

| Component of lysis mater mixture | Volume (µl) |
|---|---|
| 5X Lysis Buffer | 1.1 |
| 5X Protease Stock Solution | 1.1 |
| Total | 2.2 |

The 5× lysis buffer in the above Table 1 can be prepared according to the following Table 2:

TABLE 2

Components of 5X Lysis Buffer

| Component | Stock Concentration | 5X Master Mix Concentration | Volume (µl) |
|---|---|---|---|
| Tris-HCl (pH 8.0) | 1M | 250 mM | 250 |
| EDTA | 0.5M | 5 mM | 10 |
| TRITON X-100 | 10% | 2.5% | 250 |
| Super Q H$_2$O | | | 490 |
| Total | | | 1000 |

All reagents can be adequately mixed by gently vortexing the tube several times, followed by a brief spin in a microcentrifuge. This step can be repeated 3-5 times. The 5× lysis buffer can be stored at room temperature to prevent precipitation of the detergent.

5× protease stock solution can be prepared as follows: (i) prepare single use storage aliquots by re-suspending a protease, e.g., the QIAGEN protease, directly in the glass vial by adding 2.38 ml Super Q H$_2$O to a final concentration of 3150 mAU/ml. Ensure the protease is adequately dissolved by gently vortexing the vial several times. Aliquot the solution into 25 µl aliquots and immediately freeze at −80° C., and (ii) remove a single use storage aliquot from the freezer and thaw and prepare the 5× protease stock solution according to the Table 3 below:

TABLE 3

Components of 5X Protease Stock Solution

| Component | Stock Concentration | 5X Master Mix Concentration | Volume (µl) |
|---|---|---|---|
| QIAGEN Protease | 3150 mAU/ml | 450 mAU/ml | 15 |
| Super Q H$_2$O | | | 90 |
| Total | | | 105 |

Accordingly, the final concentration of the 5× protease stock solution is 450 mAU/ml.

(3) Add 2 µl of the lysis master mixture prepared above to each tube containing a cell, positive control genomic DNA or the negative control. Incubate the samples according to the following program in a thermal cycler: 50° C. 30 min, 70° C. 20 min, and 4° C. hold.

In some embodiments, a positive control genomic DNA is included (about 30 pg) in each experiment. A positive control genomic DNA can be prepared in a two-step serial dilution from a 10 ng/µl stock solution as prepared in Tables 4 and 5 below:

TABLE 4

Component of Intermediate Genomic DNA Dilution

| Component | Stock Concentration | Intermediate Concentration | Volume (µl) |
|---|---|---|---|
| DNA | 10 ng/µl | 100 pg/µl | 2 |
| 1X RS1 | | | 198 |
| Total | | | 200 |

Then the intermediate DNA dilution prepared according to the above table can be subsequently diluted according to the following Table 5:

TABLE 5

Component of Final Genomic DNA Dilution

| Component | Stock Concentration | Intermediate Concentration | Volume (µl) |
|---|---|---|---|
| DNA | 100 pg/µl | 10 pg/µl | 10 |
| 1X PBS | | | 90 |
| Total | | | 100 |

3 µl of the final dilution prepared in the above table can be used as input of a positive control genomic DNA. This corresponds to 30 pg or the genomic equivalent of 5 cells. More or less of genomic DNA can also be used according to the method provided herein.

Example 2 Tagmentation of Target Nucleic Acid Directly in Cell Lysate

In some embodiments, the genomic DNA in the cell lysate, e.g., as prepared in Example 1 can be tagmented (tagged and fragmented) by the Nextera transposome (available from Illumina, Inc, San Diego, Calif.). The Nextera transposome can simultaneously fragments the input DNA and adds tag/adapter sequences to the ends. The tagmentation master mixture can be directly added to the cell lysate prepared in Example 1 without any prior DNA purification or amplification step. The tagmentation master mixture can be prepared as shown in Table 6 below and the master mixture can be scaled up, e.g., 10% extra to compensate for losses during pipetting, according the number of samples.

TABLE 6

Components of Tagmentation Master Mixture

| Component | Volume (µl) |
|---|---|
| Tagmentation DNA Buffer | 11 |
| Nextera Amplicon Tagment Mixture | 2.2 |
| Super Q H$_2$O | 3.3 |
| Total | 16.5 |

The Tagmentation DNA Buffer and Nextera Amplicon Tagment Mixture are available from Illumina, Inc (San Diego, Calif.; Part No. 15027866 and 15031561). The Tagmentation DNA Buffer includes Tris(hydroxymethyl) aminomethane, MgCl2, and dimethylformamide. Nextera Amplicon Tagment Mixture includes transposome enzyme. 15 µl of the Tagmentation Master Mixture can then be added to each cell lysate, e.g., generated from Example 1, and incubated with the cell lysate at 55° C. for 5 min, and then at 4° C. to terminate the reaction. Then neutralize tagment buffer including SDS (available from Illumina, Inc, San Diego, Calif.) can be added to the tube and incubated at room temperature for 5 minutes.

Example 3 Limited-Cycle PCR Amplification

The tagmented DNA fragments, e.g., as prepared in Example 2, can be amplified by a limited-cycle PCR program. This PCR step can also add other sequences at the two ends of the tagged nucleic acid fragments, e.g., index 1 (i7) and index 2 (i5) (available from Illumina, Inc, San Diego, Calif.) and sequences required for other purposes, e.g., cluster formation. For example, the following components in Table 7 (available from Illumina, Inc, San Diego, Calif.) can be added to the neutralized tagmentation produced from Example 3.

TABLE 7

Components for Limited-Cycle PCR

| Component | Volume (µl) |
|---|---|
| PCR Master Mixture | 15 |
| Index 1 Primer (P5 primer) | 5 |
| Index 2 primer (P7 primer) | 5 |

The PCR master mixture in Table 7 can be prepared as in Table 8 below:

TABLE 8

Components of PCR Master Mixture

| Component | Stock Concentration | Master Mix Concentration | Volume (µl) |
|---|---|---|---|
| KAPA HiFi Fidelity Buffer | 5X | 3.33X | 999 |
| dNTP Pool | 25 mM each | 1.00 mM each | 59.94 |
| KAPA HiFi DNA Polymerase | 1 U/µl | 0.033 U/µl | 49.95 |
| Super Q H$_2$O | | | 391.11 |
| Total | | | 1500 |

An exemplary PCR program is as follows: 72° C. 3 min, 98° C. 30 sec, and then 20 cycles of 98° C. 10 seconds, 60° C. 30 seconds, and 72° C. 30 seconds, and finally samples are held at 4° C.

Example 4 Protease Activity is Useful for Uniform Access to DNA

The effect of protease activity on uniform access to DNA is analyzed in this example. In particular, 0 mg/ml, 0.1 mg/ml (4.5 mAU/ml), 0.5 mg/ml (22.5 mAU/ml), or 2.5 mg/ml (112.5 mAU/ml) proteases are used to treat whole cells and nuclei. The percentage of unique mapped read is analyzed for each sequencing. FIG. 1 is a histogram showing the percentage of unique mapped read in a sequencing using 0 mg/ml, 0.1 mg/ml, 0.5 mg/ml, or 2.5 mg/ml proteases treated whole cells or nuclei. As shown, the percentage of unique mapped read increases as the concentration of protease increases, and this is true using both whole cell and nuclei as starting material. It is also noted that percentage of unique mapped read using 0.5 mg/ml protease is similar to that using 2.5 mg/ml.

Figure 2:
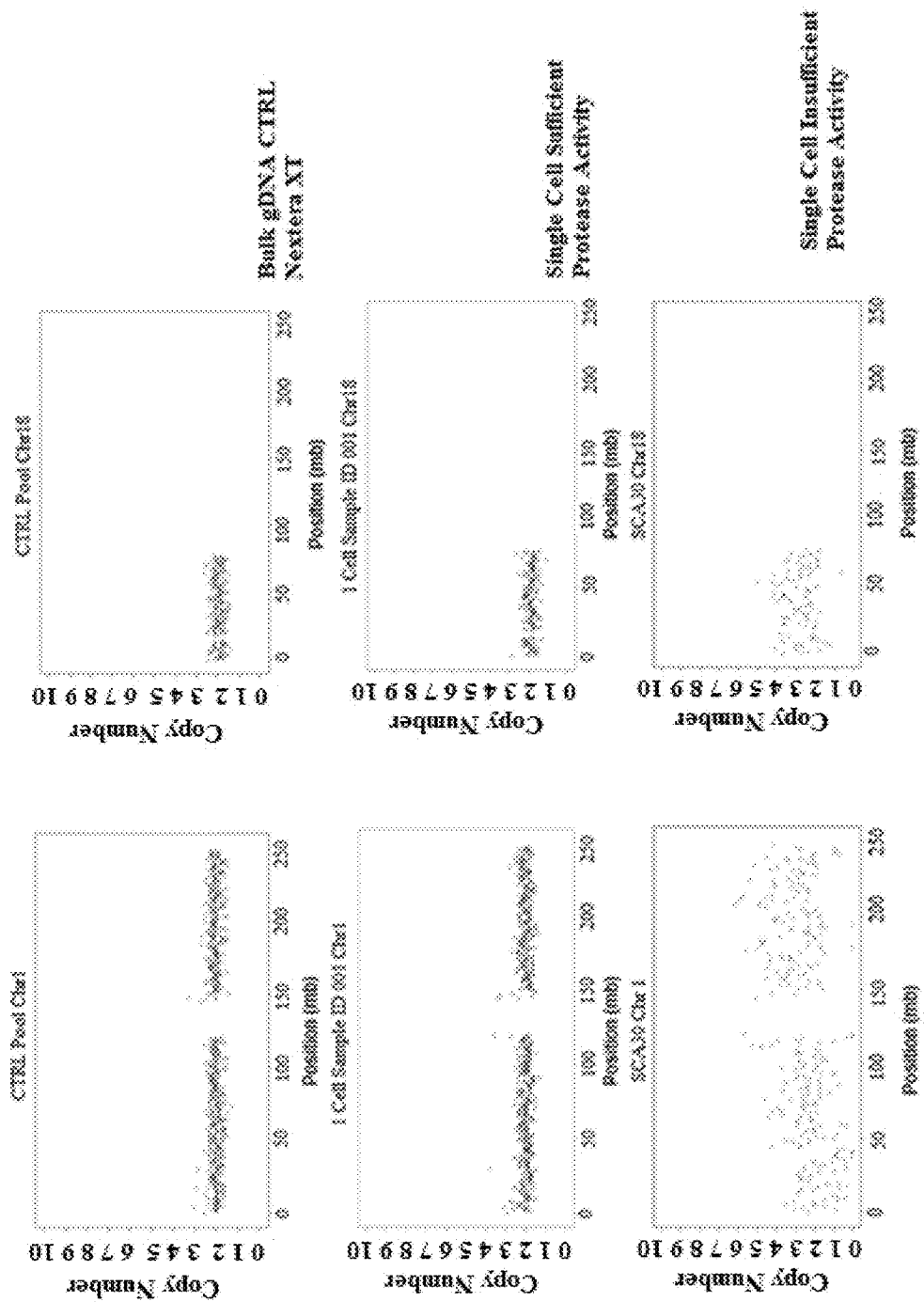
FIG. 2 show histograms of copy number analysis results using bulk DNA, single cell treated with sufficient protease activity, and single cell treated with insufficient protease activity.

The effect of protease activity on uniform access to DNA is further analyzed by comparing counts and copy number analysis results among using bulk genomic DNA control with Nextera XT library preparation, using single cell with sufficient protease activity, and using single cell with insufficient protease activity. FIG. 2 show histograms of counts and copy number analysis results using bulk DNA, single cell treated with sufficient protease activity, and single cell treated with insufficient protease activity. As shown, when relative large amount of genomic DNA is used with current Nextera XT library preparation method, as show in the upper panel of FIG. 2, relative clean copy number analysis results can be achieved with insignificant noise. When only a single cell is used for sequencing the noise is significant and the copy number analysis data shows scattered distribution pattern as shown in the lower panel of FIG. 2. Surprisingly, when the single cell is treated with sufficient protease (0.5 mg/ml), the copy number analysis results are restored to be comparable with that using bulk genomic DNA, showing clean data with insignificant noise, as shown in the middle panel of FIG. 2. This indicates that the protease can increase the accessibility of the genomic DNA by the transposase since DNA-binding proteins can be uniformly removed.

These results show that protease activity is useful for uniform access to DNA in sequencing.

Example 5 Optimize Protease Concentration

Figure 3A:
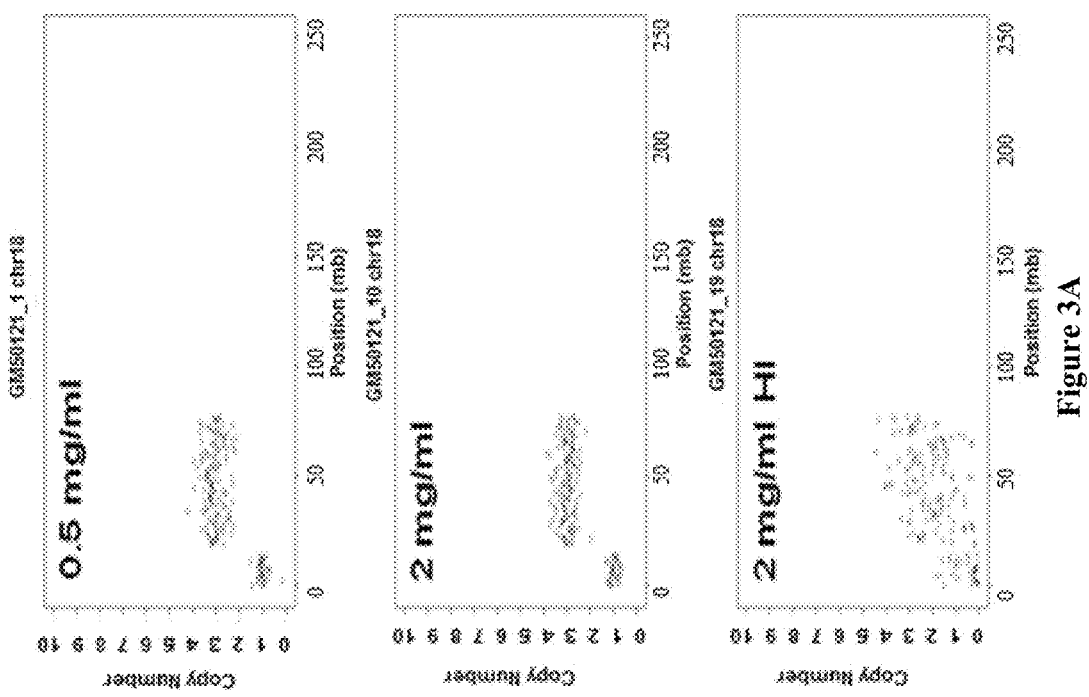
FIG. 3A shows histograms of copy number analysis results in a single cell treated with 0.5 mg/ml active protease, 2 mg/ml active protease, or 2 mg/ml pre-heat inactivated protease.

In this example, the concentration of protease used in the present method is analyzed. FIG. 3A shows histograms of copy number analysis results in a single cell treated with 0.5 mg/ml active protease, 2 mg/ml active protease, or 2 mg/ml active protease. As shown, when single cell is treated with 0.5 mg/ml or 2 mg/ml active protease, clean copy number analysis result is similarly achieved as shown in the top two histograms of FIG. 3A. In contrast, when reaction is performed with protease pre-heat inactivated at 70° C., no clean copy number result can be achieved, as shown in the bottom histogram of FIG. 3A. This result shows that protease of both 0.5 mg/ml or 2 mg/ml concentrations are effective and sufficient.

Figure 3B:
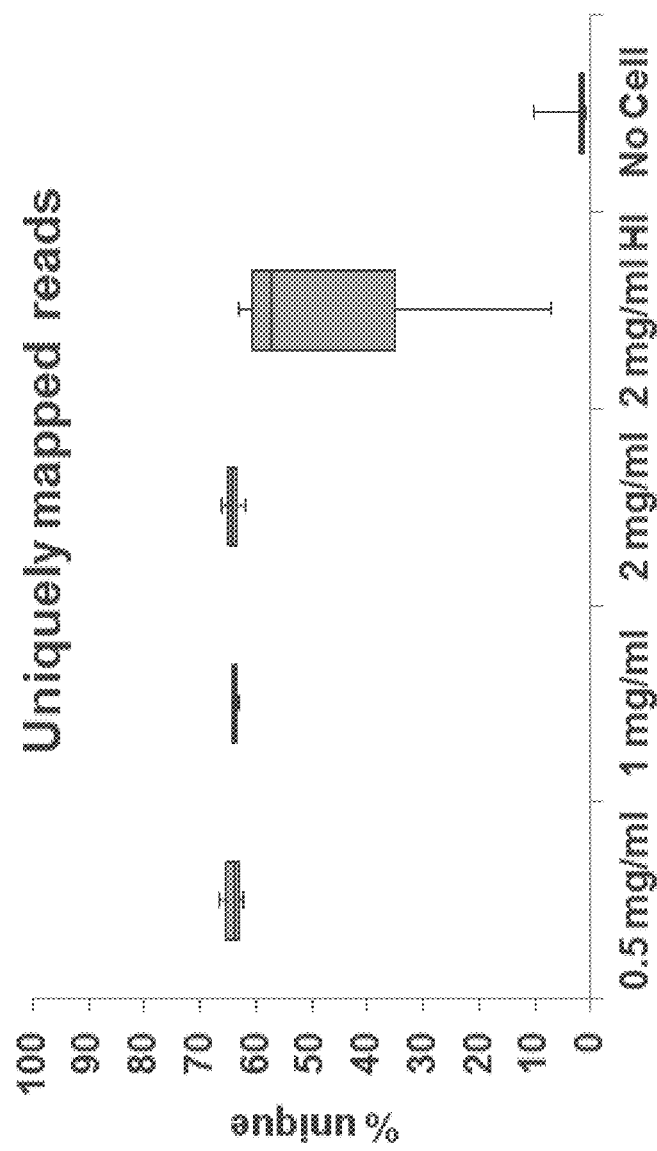
FIG. 3B shows a histogram of percentage of unique mapped read in a sequencing of a single cell treated with 0.5 mg/ml active protease, 1 mg/ml active protease, 2 mg/ml protease under reaction temperature, or 2 mg/ml pre-heat inactivated protease, and a control sample without cells.

The percentage of unique mapped read is also analyzed in a sequencing of a single cell treated with 0.5 mg/ml active protease, 1 mg/ml active protease, 2 mg/ml active protease, or 2 mg/ml pre-heat inactivated (at 70° C.) protease. FIG. 3B shows a histogram of percentage of unique mapped read in a sequencing of a single cell treated with 0.5 mg/ml active protease, 1 mg/ml active protease, 2 mg/ml active protease, or 2 mg/ml pre-heat inactivated protease, and a control sample without cells. As shown, the percentages of unique mapped reads in sequencing using a single cell treated with 0.5 mg/ml active protease, 1 mg/ml active protease, and 2 mg/ml active protease are all about 65% with small variation. In contrast, when protease is inactivated under 70° C., even if higher amount of protease is used, the percentage of unique mapped read is much lower with huge variations.

Figure 3C:
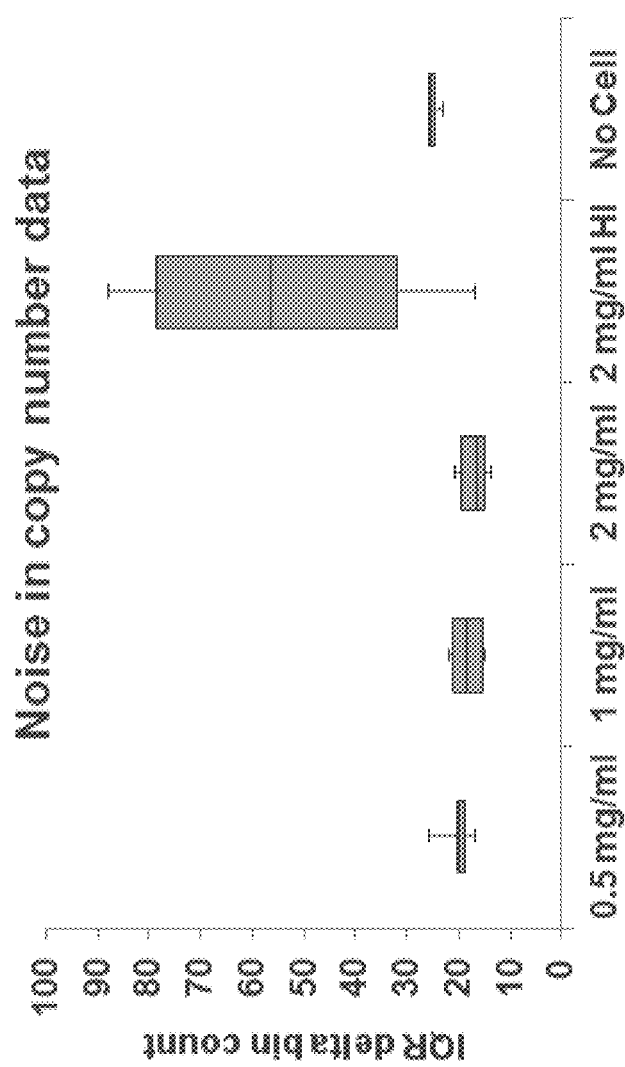
FIG. 3C shows a histogram of read count differences between neighboring bins (Inter Quartile Range of read count difference between neighboring bins) in a sequencing of a single cell treated with active 0.5 mg/ml protease, 1 mg/ml active protease, 2 mg/ml active protease, or 2 mg/ml pre-heat inactivated protease, and a control sample without cells.

In addition, the noise in copy number data is analyzed by analyzing count differences between neighboring bin count. FIG. 3C shows a histogram of read count differences between neighboring bins (Inter Quartile Range of read count difference between neighboring bin) in a sequencing of a single cell treated with 0.5 mg/ml active protease, 1 mg/ml active protease, 2 mg/ml active protease, or 2 mg/ml pre-heat inactivated protease, and a control sample without cells. As shown, count differences between neighboring bin count in a sequencing using a single cell treated with 0.5 mg/ml active protease, 1 mg/ml active protease, and 2 mg/ml active protease are all relatively small (about 20%) with small variation. In contrast, when protease is inactivated under 70° C., even if higher amount of protease (2 mg/ml) is used, count difference between neighboring bin count is much bigger with huge variations.

Collectively, these results show that protease with concentration range from 0.5 mg/ml to 2.0 mg/ml (22.5 mAU/ml to 90 mAU/ml) is sufficient and effective in the method provided herein.

Example 6 Optimize PH Condition of Protease Digestion Reaction

In this example, the pH condition of protease digestion reaction is optimized balancing the protease activity and sequencing results.

Figure 4A:
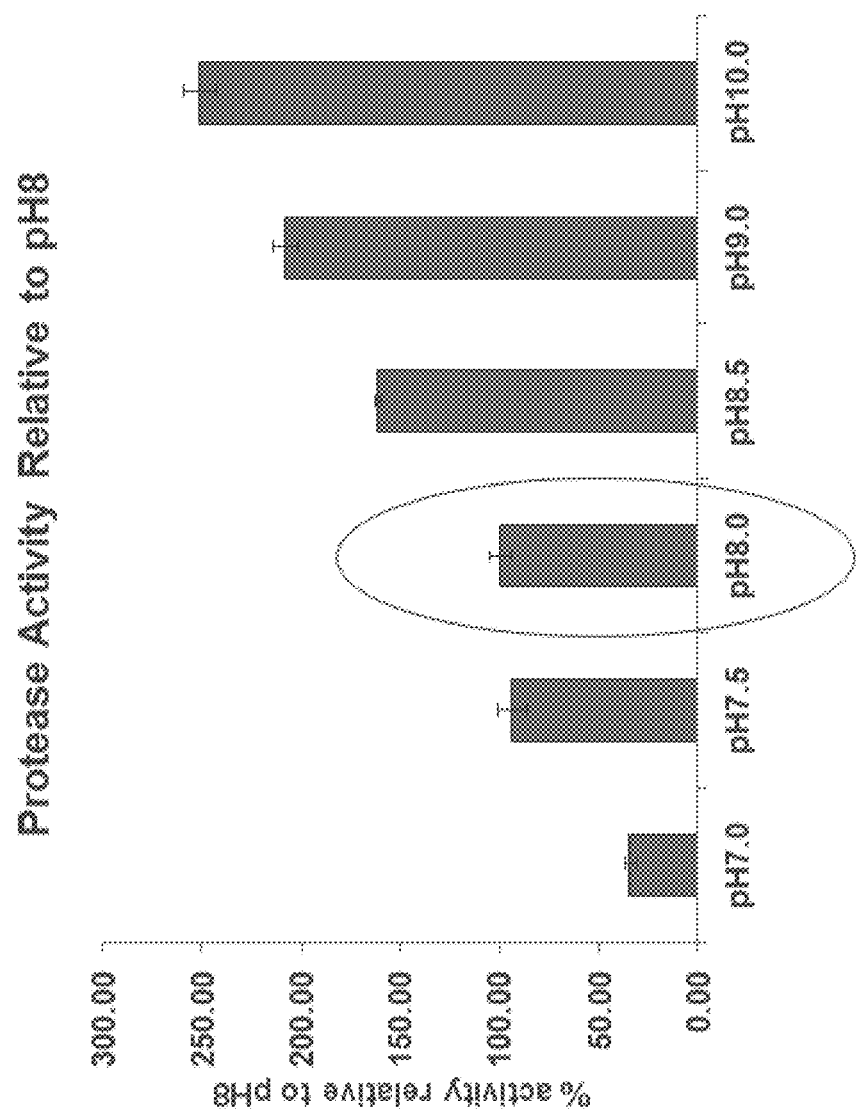
FIG. 4A is a histogram showing relative activity of protease under pH 7.0, pH 7.5, pH 8.0, pH 8.5, pH 9.0, or pH 10.0.

The protease activity is analyzed under different pH conditions. The result is shown in FIG. 4A. FIG. 4A is a histogram showing relative activity (relative to protease activity at pH 8.0) of protease under pH 7.0, pH 7.5, pH 8.0, pH 8.5, pH 9.0, or pH 10.0. As shown, the activity of protease increase as pH value increases with protease having lowest activity at pH 7.0 and highest activity at pH 10.0.

Figure 4B:
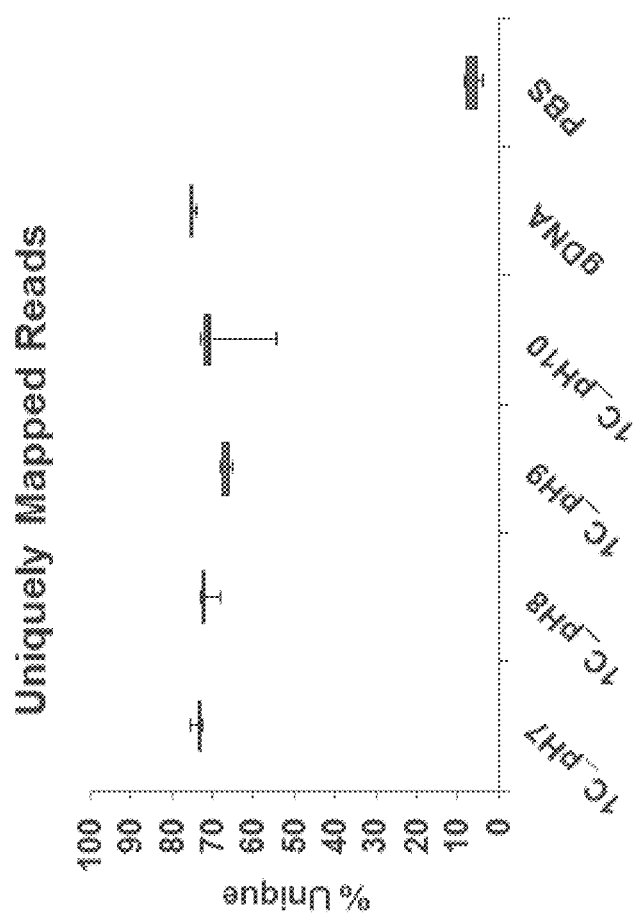
FIG. 4B shows a histogram of percentage of unique mapped reads in a sequencing experiment of a single cell treated with protease under pH 7.0, pH 8.0, pH 9.0, or pH 10.0.

The percentage of unique mapped read is then analyzed under various pH conditions. FIG. 4B shows a histogram of percentage of unique mapped read in a sequencing of a single cell treated with protease under pH 7.0, pH 8.0, pH 9.0, or pH 10.0. As shown, when pH is 7, 8 or 9, about 70% clean unique mapped reads can be achieved. However, when pH is 10, less percentage of unique mapped reads can be achieved and the data variation increases significantly.

Figure 4C:
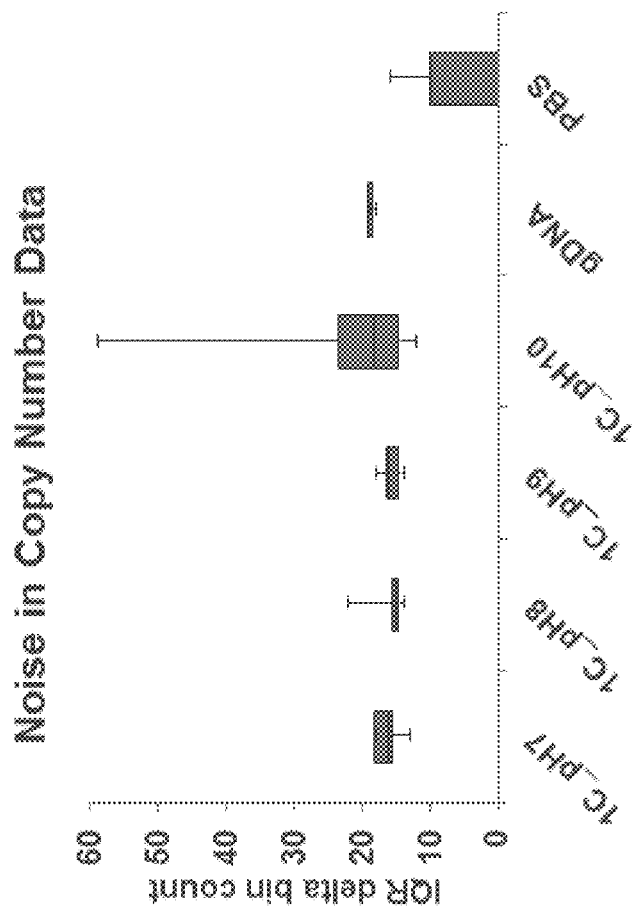
FIG. 4C shows a histogram of read count differences between neighboring bins (Inter Quartile Range of read count difference between neighboring bins) in a sequencing experiment of a single cell treated with protease under pH 7.0, pH 8.0, pH 9.0, or pH 10.0.

The noise in copy number data is also analyzed by comparing count differences between neighboring bins. FIG. 4C shows a histogram of read count differences between neighboring bins (Inter Quartile Range of read count difference between neighboring bin) in a sequencing of a single cell treated with 0.5 mg/ml protease under pH 7.0, pH 8.0, pH 9.0, or pH 10.0. As shown, consistent with the unique mapped read results, count differences between neighboring bins are relatively small (about 20%) with small variations; while count differences between neighboring bins are significantly increased with huge variation at pH 10.0.

In some embodiments, the pH value of the digestion reaction is between pH 7.0 to pH 9.0.

Example 7 Test Heat Inactivation of Protease

In some embodiments, the protease provided herein can be heat inactivated. As discussed above, in prepared embodiments, the protease can be inactivated under relatively low temperature (e.g. 70° C.) so that the double stranded DNA conformation can be preserved for the tagmentation reaction. In this example, the protease (from QIAGEN) is analyzed for heat inactivation and its effect on sequencing results.

Figure 5A:
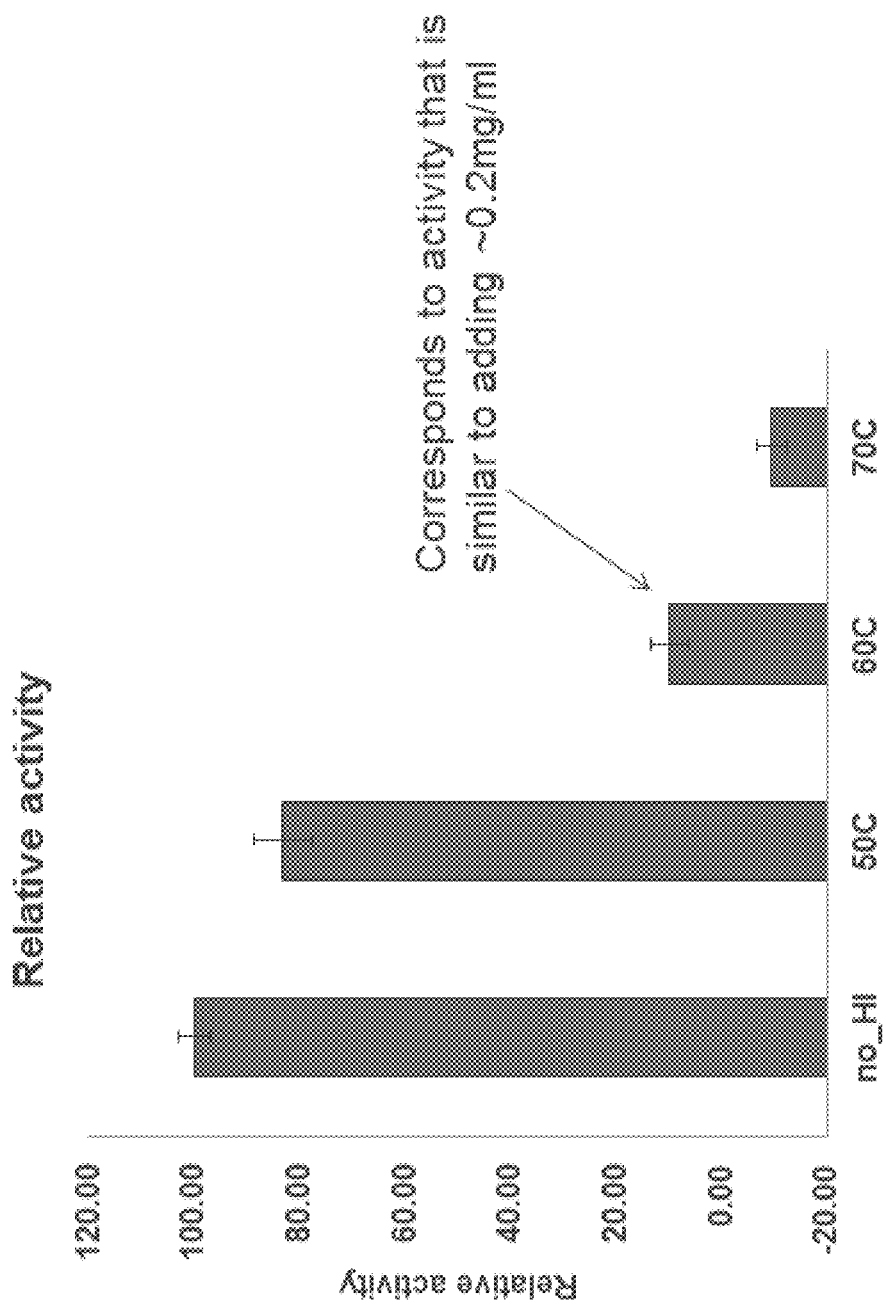
FIG. 5A is a histogram showing relative protease activity pre-heated at room temperature, 50° C., 60° C., or 70° C.

The protease was pre-heated at different temperatures, and the activity of the protease was tested. The result is shown in FIG. 5A, showing a histogram of relative protease activity when pre-heated at room temperature, 50° C., 60° C., or 70° C. As shown, the protease activity progressively decreases as the temperature increases, and is completely inactivated at 70° C. This result is consistent with results shown in Example 5 above.

Figure 5B:
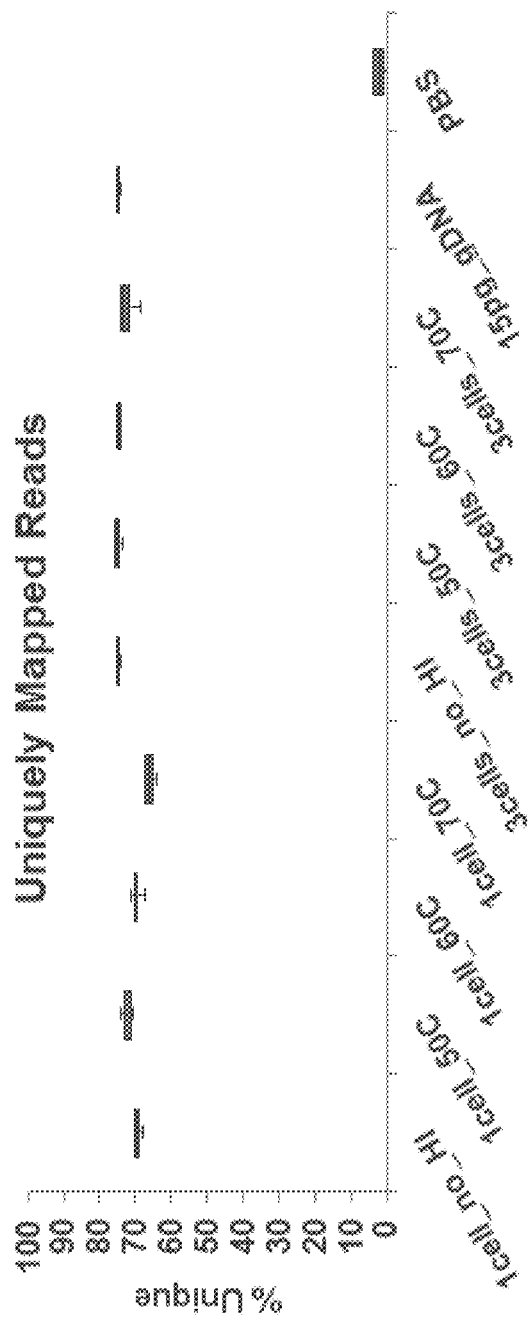
FIG. 5B shows a histogram of percentage of unique mapped reads in a sequencing experiment of a single cell, three cells, or 15 pg genomic DNA, treated with protease pre-heated at room temperature, 50° C., 60° C., or 70° C.

The percentage of unique mapped read in sequencing of a single cell, three cells, and 15 pg genomic DNA at various temperatures are analyzed. FIG. 5B shows a histogram of percentage of unique mapped read in a sequencing of a single cell, three cells, or 15 pg genomic DNA, treated with 2.0 mg/ml protease at room temperature, 50° C., 60° C., or 70° C. As shown, the percentage of unique mapped read decrease as temperature increases. However, because relatively higher concentration of protease (2.0 mg/ml) is used in the experiment, there is more tolerance for reduced protease activity at 70° C. As such, the percentage of unique mapped read at 70° C. is still relative high even though lower than those treated under lower temperatures.

Figure 5C:
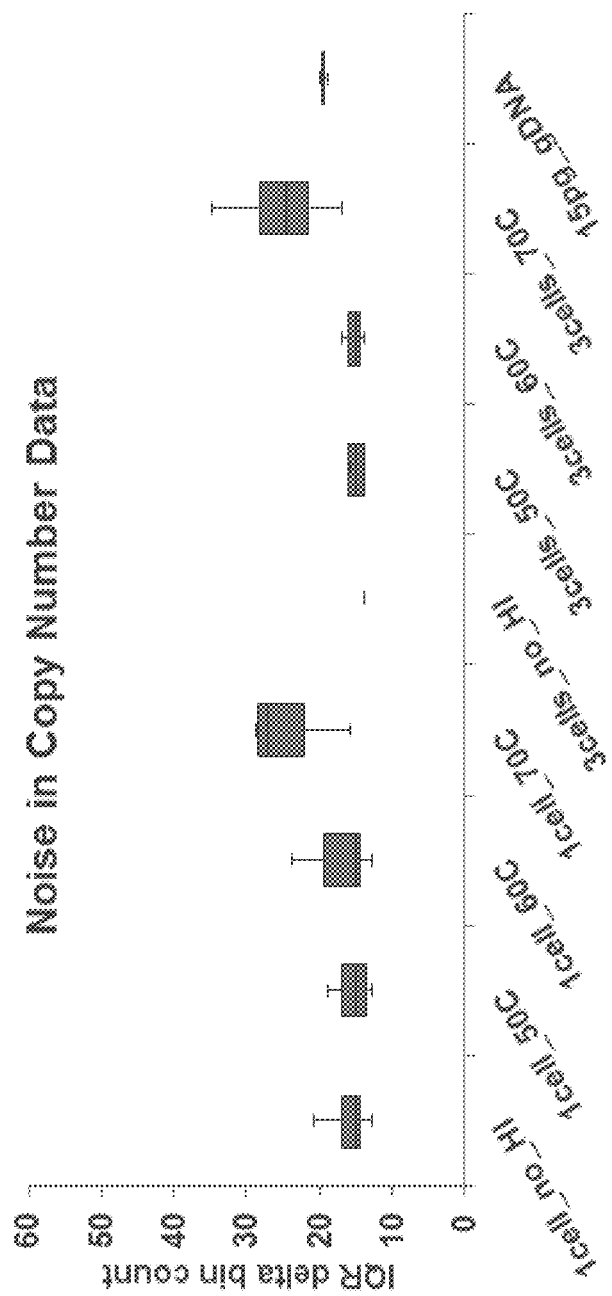
FIG. 5C shows a histogram of read count differences between neighboring bins (Inter Quartile Range of read count difference between neighboring bin) in a sequencing experiment of a single cell, three cells, or 15 pg genomic DNA, treated with protease pre-heated at room temperature, 50° C., 60° C., or 70° C.

The count differences between neighboring bins in sequencing of a single cell, three cells, and 15 pg genomic DNA at various temperatures are also analyzed. FIG. 5C shows a histogram of read count differences between neighboring bins (Inter Quartile Range of read count difference between neighboring bin) in a sequencing of a single cell, three cells, or 15 pg genomic DNA, treated with 2 mg/ml protease at room temperature, 50° C., 60° C., or 70° C. As shown, the count differences between neighboring bins are relatively small with small variations at lower temperature (e.g., at room temperature and 50-60° C.); while the count differences between neighboring bins are significantly increased with bigger variation at 70° C.

Example 8 Diversity of Library Increases with Smaller Inert Sizes

Figure 6A:
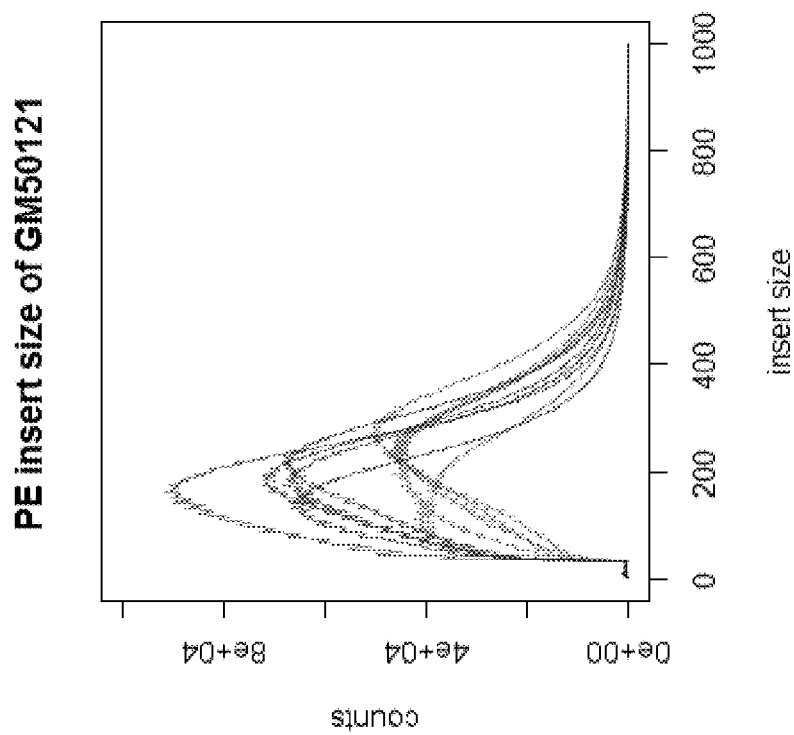
FIG. 6A shows insert size of a library generated with treatment of 1 μl Tn5 or 2 μl Tn5.
Figure 6B:
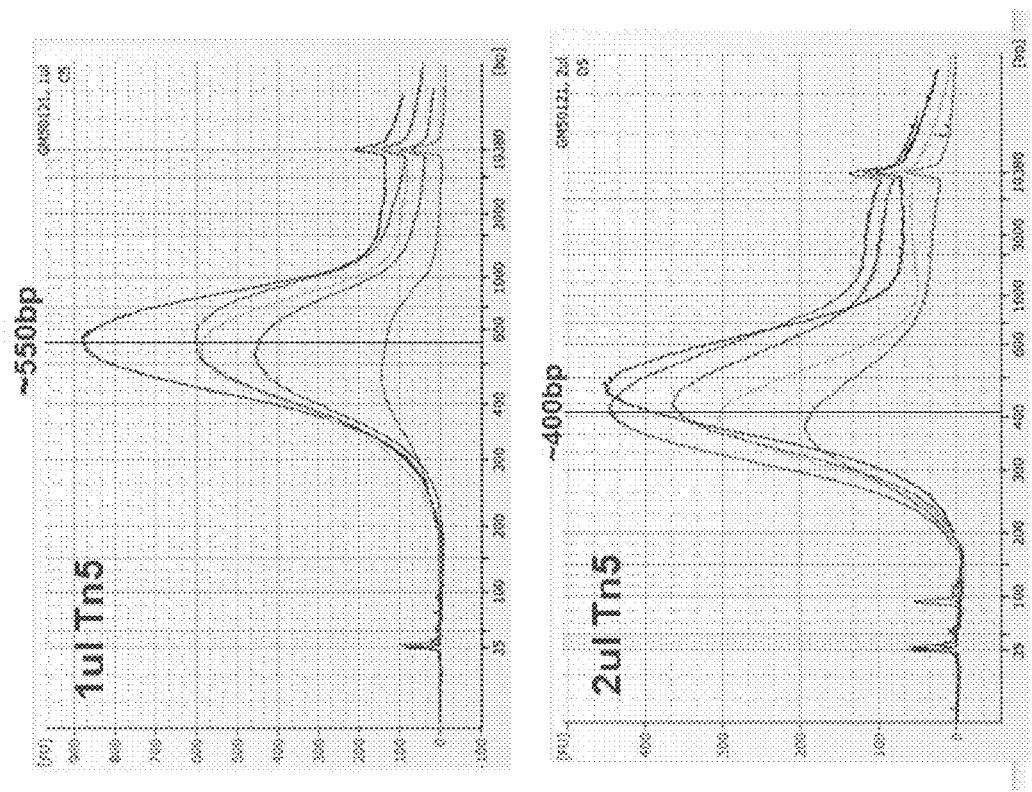
FIG. 6B shows insert size of a library generated with treatment of 1 μl Tn5 or 2 μl Tn5.
Figure 6C:
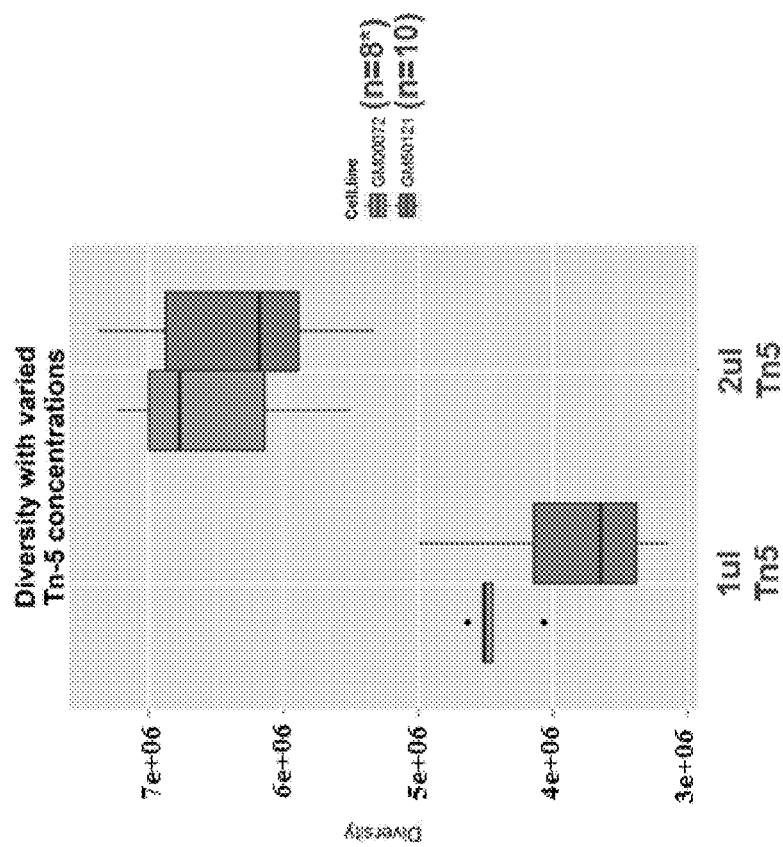
FIG. 6C shows diversity of libraries generated with treatment of 1 μl Tn5 or 2 μl Tn5.

In a single-cell sequencing, only two copies of genome are present, and thus smaller insert size tends to increase library diversity. As shown in FIG. 6A, the counts, and thus the diversity represented by a library, increase as the insert size decreases. Therefore, in some embodiments, the method herein use higher amount of transposase in the tagmentation step to increase fragmentation and reduce insert size of the tagged nucleic acid fragments. FIG. 6B shows insert size of a library treated with 1 µl Tn5 or 2 µl Tn5. As shown, when 1 µl Tn5 is used in a tagmentation reaction, the average fragment size is about 550 bp; while when 2 µl Tn5 is used in a tagmentation reaction, the average fragment size is about 400 bp. Consistent with smaller insert size, library diversity increases when treated with 2 µl Tn5 compared with that treated with 1 µl Tn5, as shown in FIG. 6C.

Example 9 Optimize PCR Cycles

Figure 7:
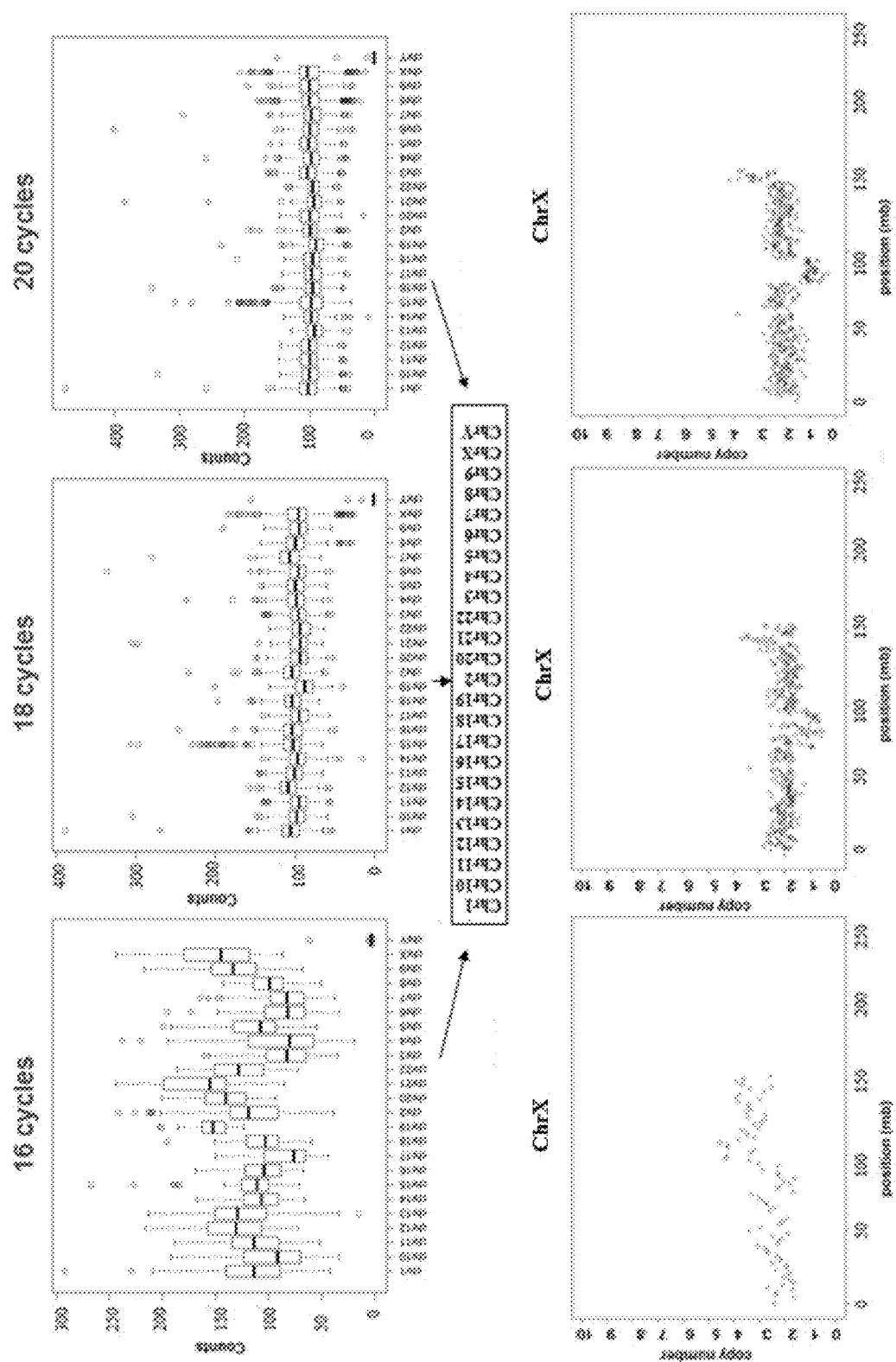
FIG. 7 shows histograms of counts and copy number analysis results in a sequencing experiment of a single cell according to the method provided herein using PCR with 16 cycles, 18 cycles, or 20 cycles.

In a sequencing using a minimal population of cells, the input DNA is relative small, and thus the cycle number of PCR can be adjusted to achieve better sequencing results. In this example, the cycle number of PCR is tested and optimized using a single cell as starting material. FIG. 7 shows histograms of counts and copy number analysis results in a sequencing of a single cell according to the method provided herein using PCR with 16 cycles, 18 cycles, or 20 cycles. As shown, the noise is big when PCR with 16 cycles is used, and the noise is significantly reduced when PCR with 18 cycles or 20 cycles is used.

Example 10 Read Distribution Using One, Three, or Five Cells

Figure 8A:
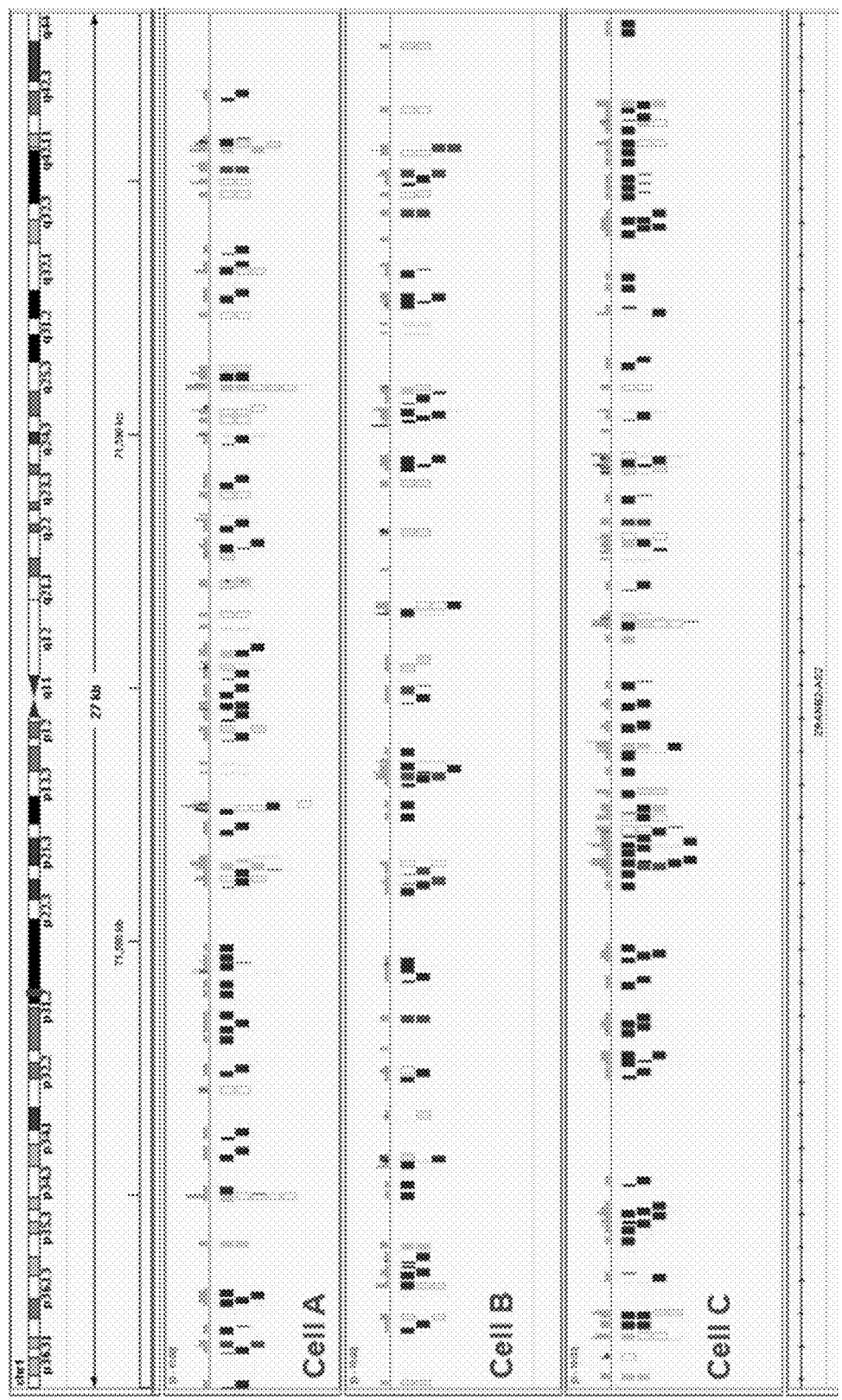
FIG. 8A shows read distribution of three single-cell sequencing experiments.
Figure 8B:
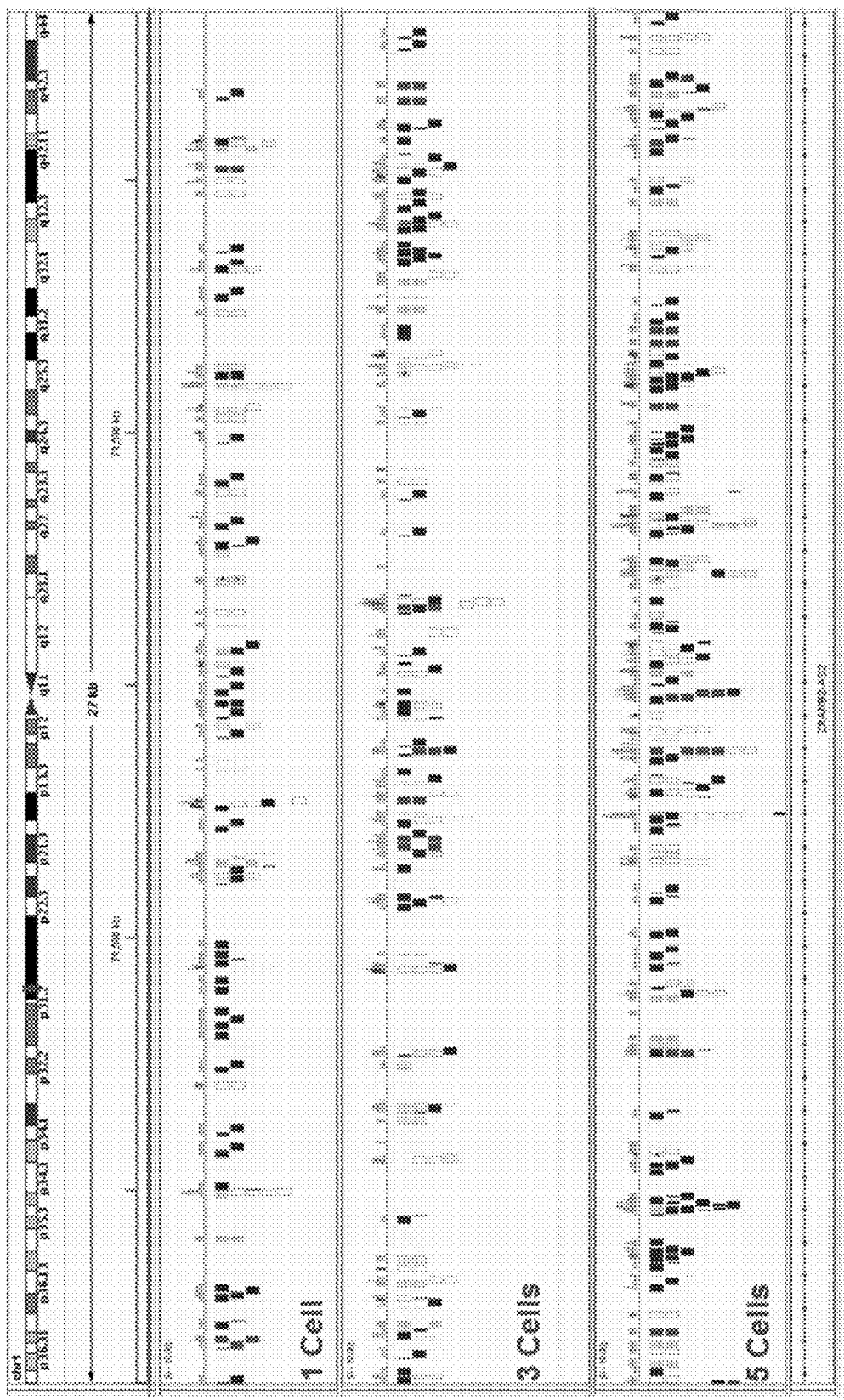
FIG. 8B shows read distribution of single-cell sequencing, three-cell sequencing, or five-cell sequencing.
Figure 8C:
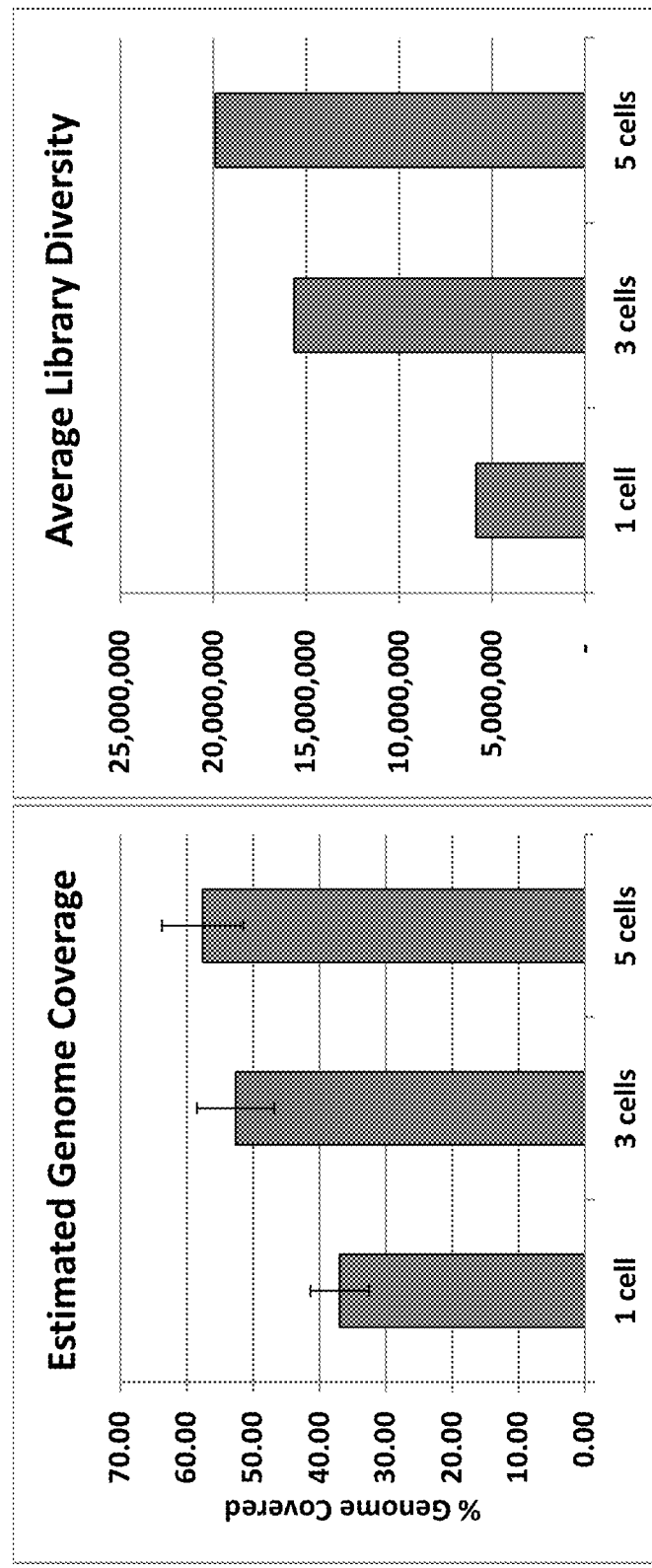
FIG. 8C shows histograms of average library diversity and estimated genome coverage using a single cell, three cells or five cells.

The read distribution using one, three or five cells in analyzed in this example. FIG. 8A shows read distribution of three single-cell sequencing. As shown, the read regions are not completed overlapped among the three single-cell sequencing. Therefore, increase cell numbers can help with broader coverage. FIG. 8B shows read distribution of single-cell sequencing, three-cell sequencing, or five-cell sequencing. As shown, genomic coverage increases as the cell number increases. FIG. 8C shows histograms of average library diversity and estimated genome coverage using a single cell, three cells or five cells. As shown, it is estimated that one cell can cover about 40% of the genome, and three cells can cover more than 50% of genome, and five cells can cover about 60% of the genome. The average library counts using one cell, three cells, and five cells are about 5 million, 15 million, and 20 million, respectively.

Figure 8D:
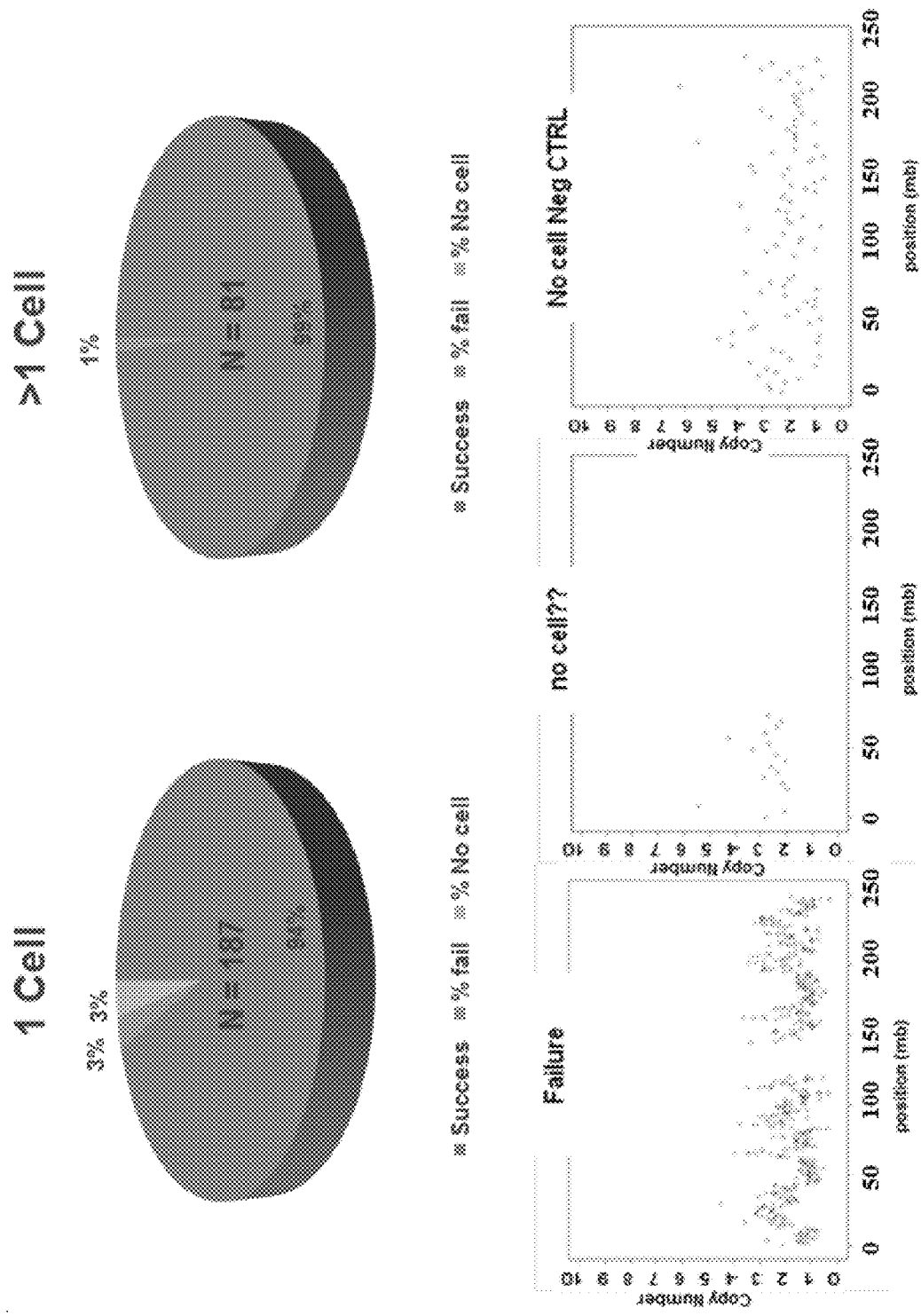
FIG. 8D shows overall protocol success rate.

FIG. 8D shows the overall success rate. As shown, when more than one cell is used, the overall success rate is 99% (N=81). When a single cell is used, the overall success rate is also relatively high 94% (N=187).

Example 11 Comparison of Counts and Copy Number Data Among Different Library Preparation Methods In this example, the method provided herein is compared with some current single cell preparation methods.

Figure 9A:
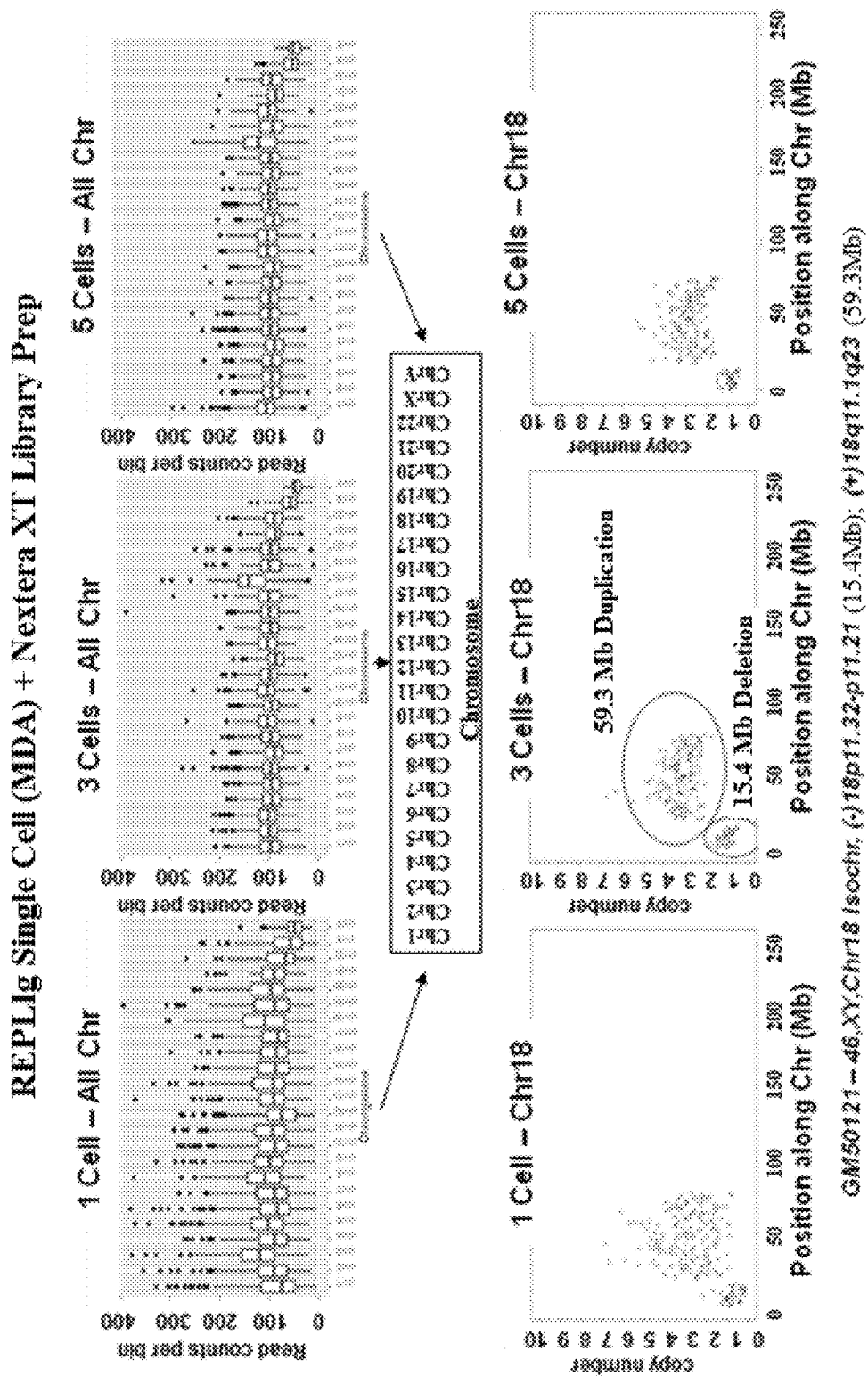
FIG. 9A shows copy number analysis using REPLIg Single Cell (MDA) with Nexteral XT library preparation.

FIG. 9A shows copy number analysis using REPLIg Single Cell (MDA) with Nexteral XT library preparation. The REPLI-g Single Cell Kit developed by QIAGEN is specially designed to amplify genomic DNA from single cells (1 to <1000 cells) or purified genomic DNA with genome coverage. The REPLI-g Single Cell Kit developed by QIAGEN uses Multiple Displacement Amplification (MDA) technology. See Spits et al., 2006, Whole-genome multiple displacement amplification from single cells, *Nature protocols* 1 (4): 1965-70. However, due to MDA introduced over-amplification bias, the copy number variation data is very noisy when derived from a single cell, three cells or five cells, as shown in FIG. 9A.

Figure 9B:
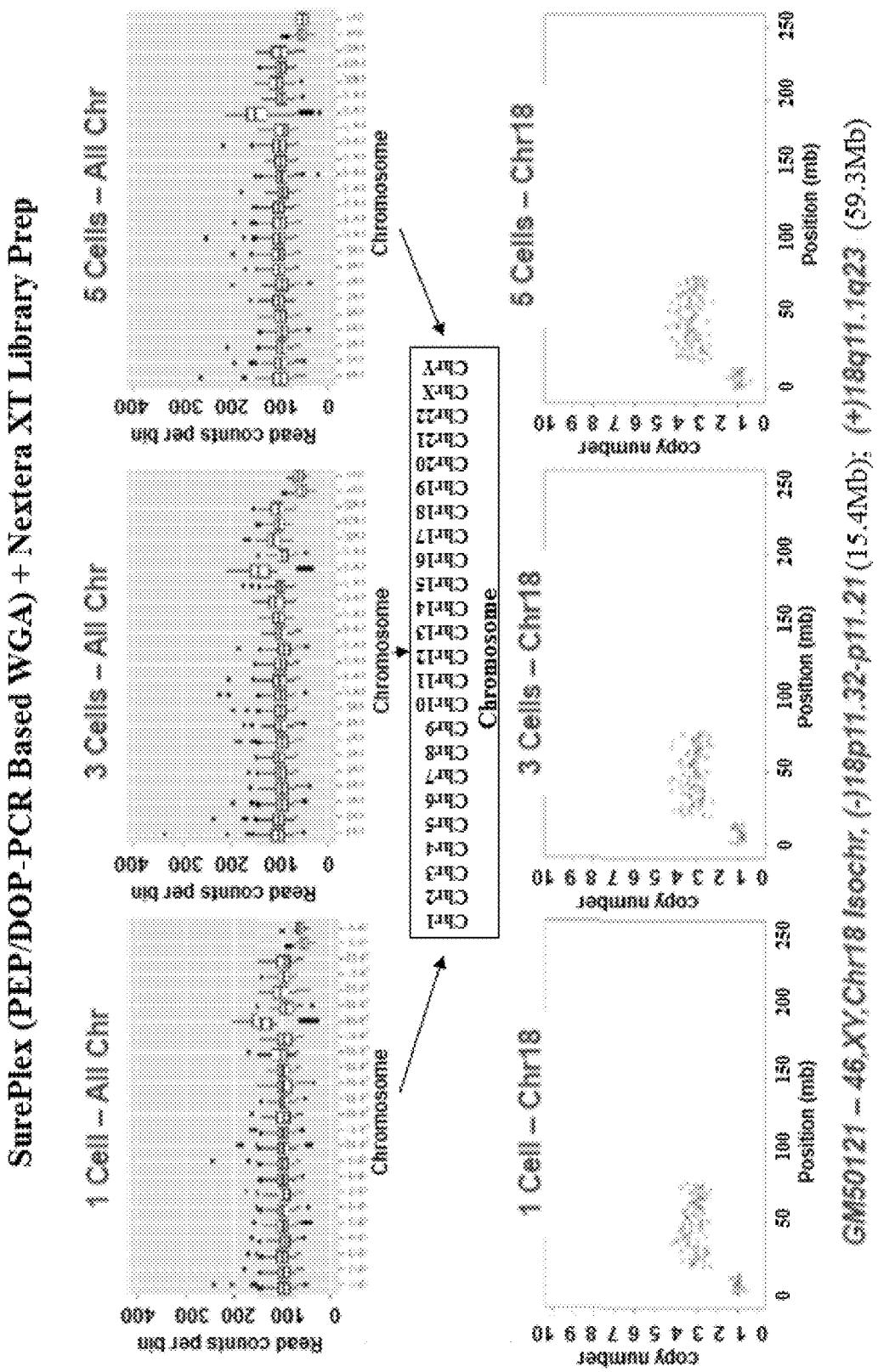
FIG. 9B shows copy number analysis using SurePlex with Nexteral XT library preparation.

FIG. 9B shows copy number analysis using SurePlex (PicoPlex) with Nexteral XT library preparation. SurePlex Amplification System developed by Illumina, Inc (San Diego, Calif.) is a solution for the extraction and amplification of DNA from single or few single cells. As shown, SurePlex Amplification System significantly reduces noise compared with MDA.

Figure 9C:
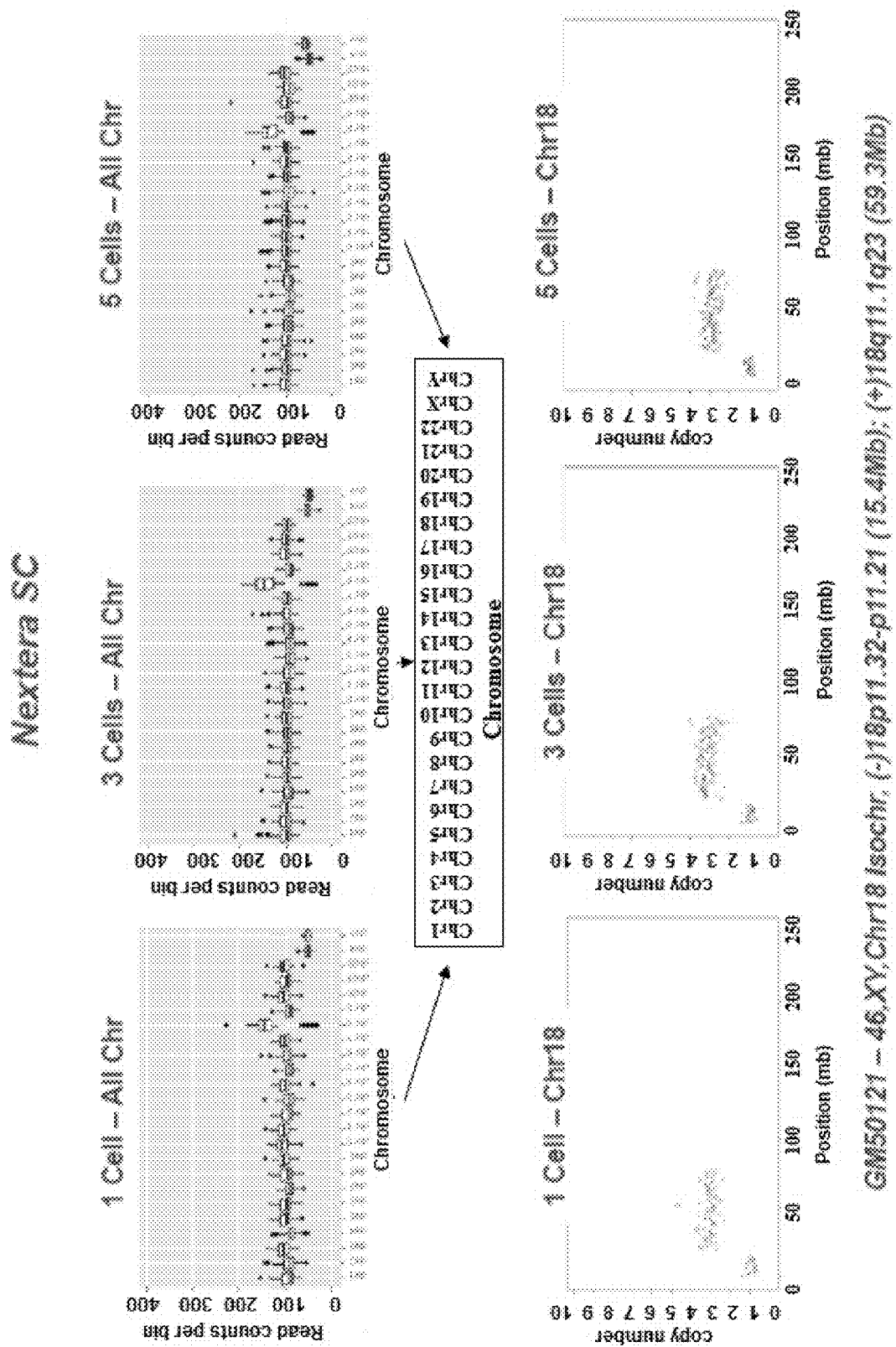
FIG. 9C shows copy number analysis using Nextera Single Cell provided herein.

FIG. 9C shows copy number analysis using a method (Nextera SC) provided herein. As shown, the noise is further reduced compared with using SurePlex Amplification System.

Example 12 Detection of Mosaicism

Figure 10A:
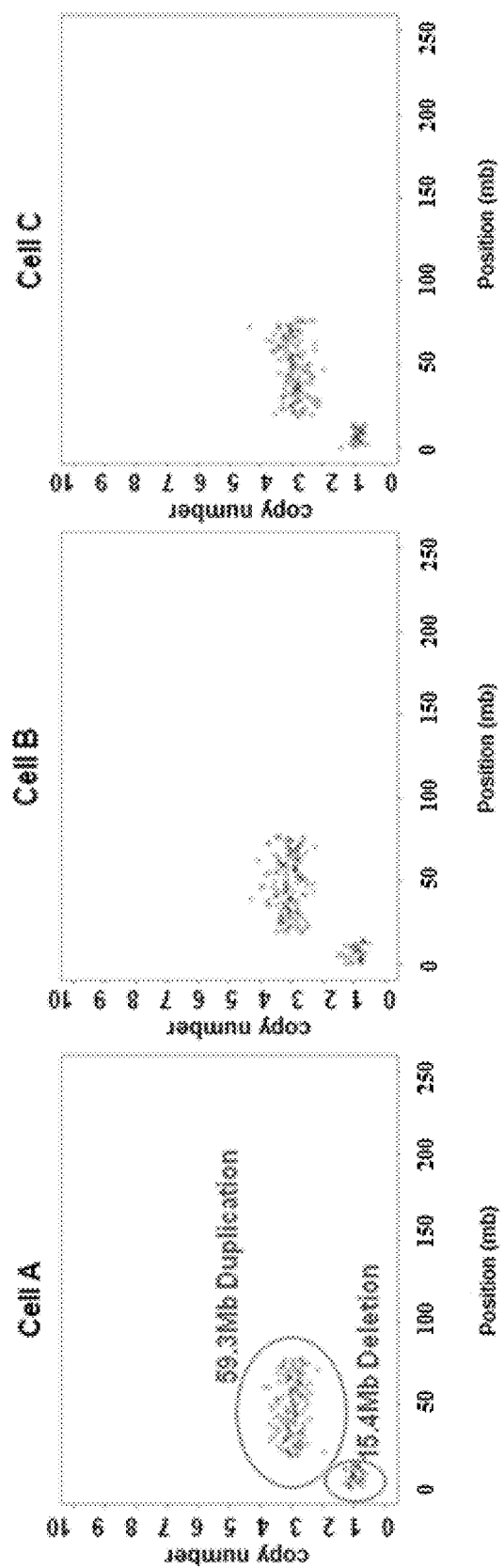
FIG. 10A shows copy number analysis data of chromosome 18 using three relicates of a single GM50121 cell.
Figure 10B:
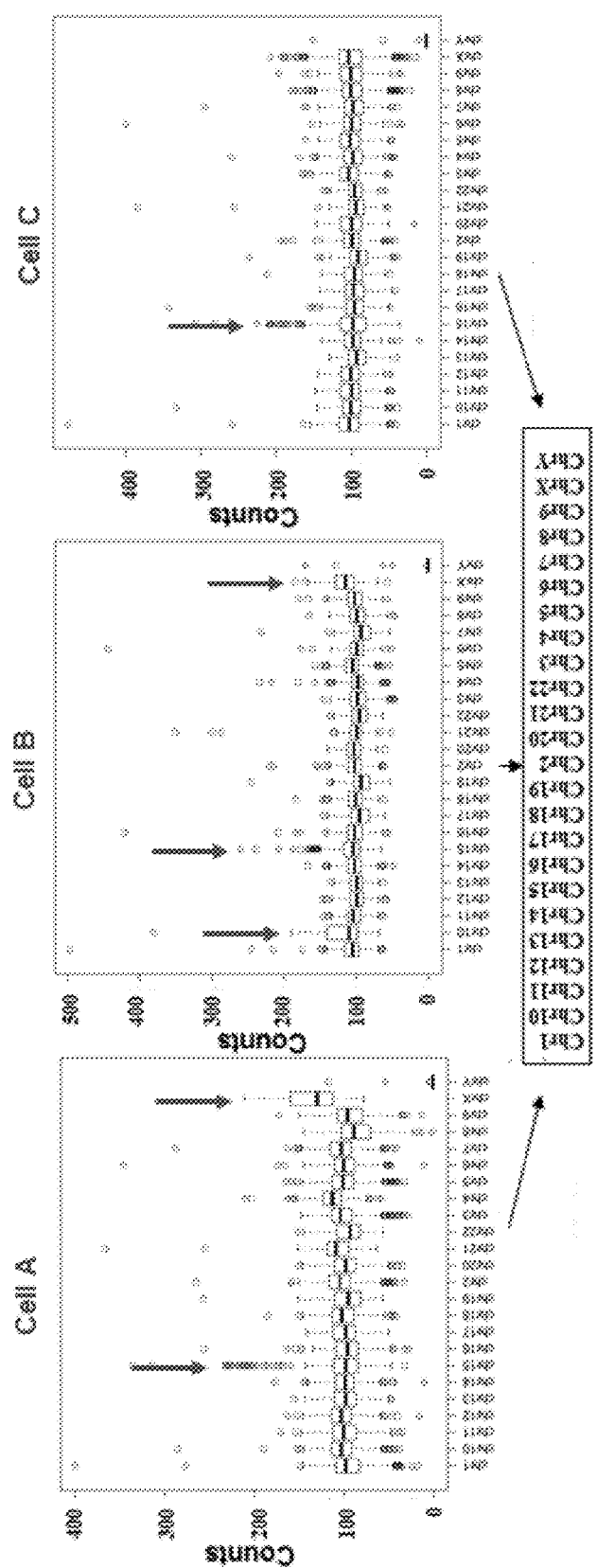
FIG. 10B shows count number data using three replicates of a single GM20916 cell.
Figure 10C:
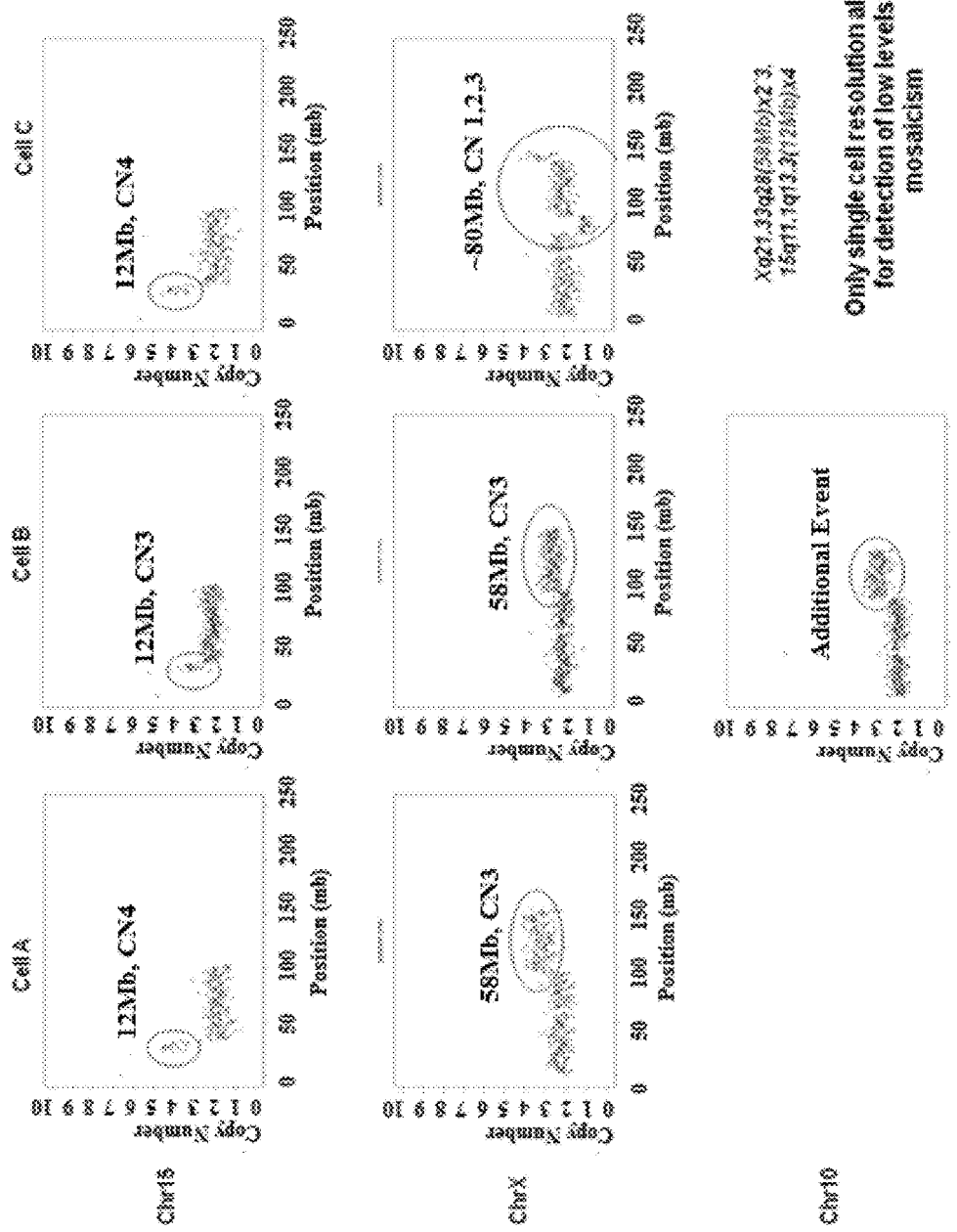
FIG. 10C shows copy number analysis data of chromosomes 15, X, and 10 using three replicates of a single GM20916 cell.
Figure 10D:
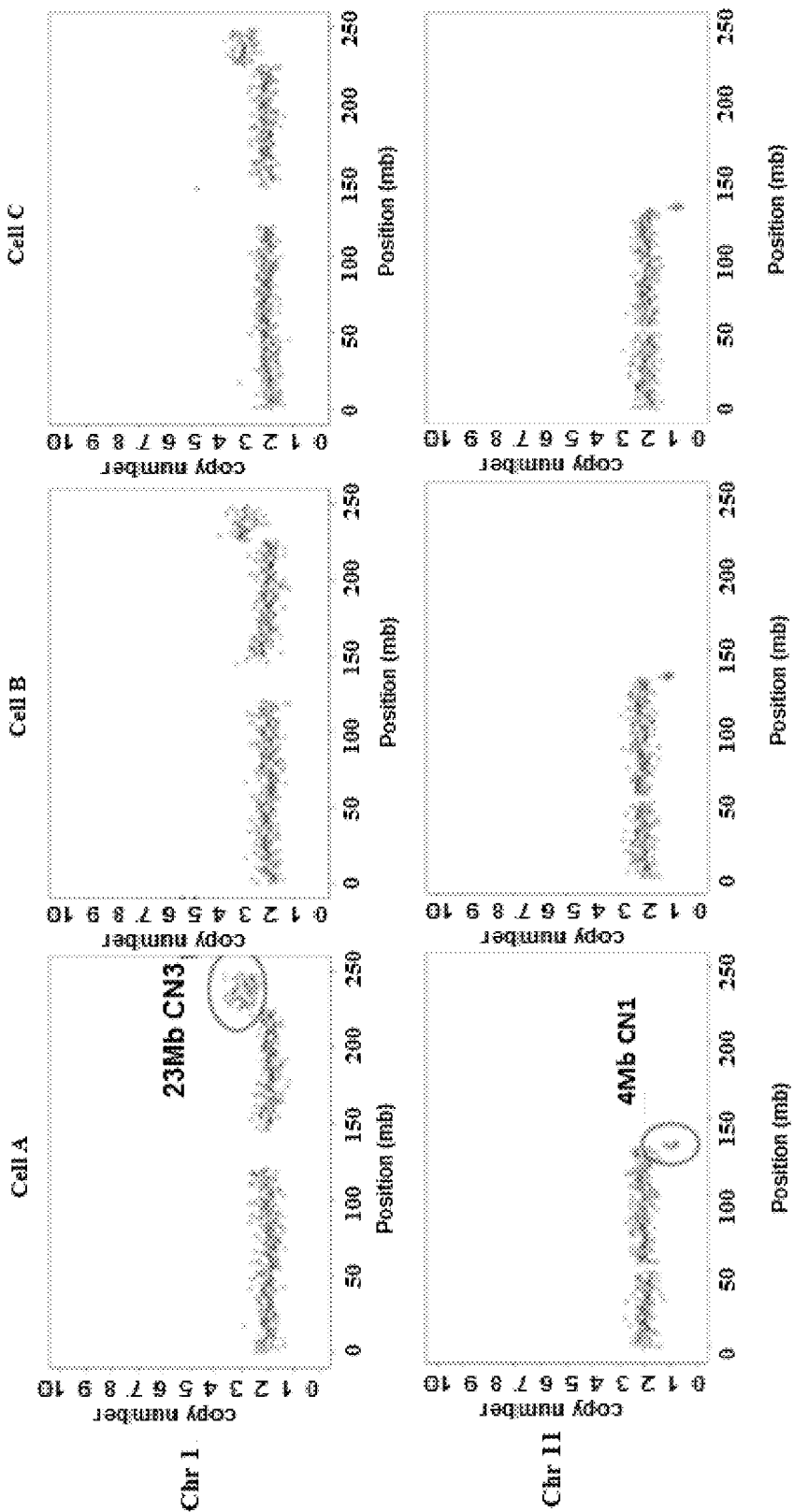
FIG. 10D shows copy number analysis data of chromosomes 1 and 11 using three replicates of a single GM10239 cell.

In this example, using the method provided herein to detect mosaicism is exemplified. FIG. 10A shows copy number analysis data of chromosome 18 using a single GM50121 cell. Copy number data from three single-cell sequencing are shown. A population representing 15.4 MB DNA is detected in each single-cell sequencing. FIG. 10B shows count number data of using a single GM20916 cell. As shown, the arrows indicate the counts originated from mosaicism. FIG. 10C shows copy number analysis data of chromosomes 15, X, and 10 using a single GM20916 cell. The copy number data for each chromosome analyzed detects an additional population representing another chromosome. Similarly, FIG. 10D shows copy number analysis data of chromosomes 1 and 11 using a single GM10239 cell. As shown in these figures, the copy number data for each chromosome analyzed in FIG. 10D also detects an additional population representing another chromosome.

A number of embodiments have been described. Nevertheless, it will be understood that various modifications may be made. Accordingly, other embodiments are within the scope of the following claims.

What is claimed is:

1. A method of preparing a library of tagged nucleic acid fragments comprising:
   (a) contacting a population of cells consisting of a single cell, directly with a lysis reagent to generate a cell lysate, wherein the lysis reagent comprises one or more proteases, and wherein the cell lysate contains a target nucleic acid;
   (b) inactivating the one or more proteases to form an inactivated cell lysate; and (c) directly applying at least one transposase and at least one transposon end composition containing a transferred strand to the inactivated cell lysate under conditions where the target nucleic acid and the transposon end composition undergo a transposition reaction to generate a mixture;

wherein the target nucleic acid comprises double-stranded DNA;

wherein:
(i) the target nucleic acid is fragmented to generate a plurality of target nucleic acid fragments, and
(ii) the transferred strand of the transposon end composition is joined to 5' ends of each of a plurality of the target nucleic acid fragments to generate a plurality of 5' tagged target nucleic acid fragments;

wherein the target nucleic acid remains double-stranded DNA for the duration of (a) through (c); and wherein no DNA purification or amplification occurs between (a) and (c).

2. The method of claim 1, wherein the one or more proteases is selected from the group consisting of a subtilisin J, a subtilisin S41, a subtilisin Sendai, a subtilisin GX, a subtilisin E, a subtilisin BL, a subtilisin Carlsberg, a subtilisin DY, and a serine endopeptidase.

3. The method of claim 1, wherein the concentration of the one or more proteases in the cell lysate is 4.5 mAU/ml to 500 mAU/ml.

4. The method of claim 3, wherein the concentration of the one or more proteases in the cell lysate is 22.5 mAU/ml.

5. The method of claim 1, wherein the population of cells are contacted with the lysis reagent at pH 7.0 to pH 10.0 in (a).

6. The method of claim 5, wherein the population of cells are contacted with the lysis reagent at pH 7.0 to pH 9.0.

7. The method of claim 1, wherein the one or more proteases are inactivated by increasing the temperature in (b).

8. The method of claim 7, wherein the one or more proteases are inactivated by increasing the temperature to 50° C.–80° C.

9. The method of claim 8, wherein the one or more proteases are inactivated by increasing the temperature to 70° C.

10. The method of claim 1, wherein the one or more proteases are inactivated by adding one or more inhibitors of the one or more proteases.

11. The method of claim 1, wherein the lysis reagent comprises one or more detergents.

12. The method of claim 11, wherein the one or more detergents are nonionic detergents.

13. The method of claim 1, wherein the target nucleic acid comprises genomic DNA, chromosomal DNA or a fragment thereof, a genome, or a partial genome.

14. The method of claim 1, wherein the at least one transposase comprises a Tn5 transposase.

15. The method of claim 1, wherein the at least one transposon end composition comprises a Tn5 transposon end.

16. The method of claim 1, wherein the transferred strand comprises tag domains containing one or more of a restriction site domain, a capture tag domain, a sequencing tag domain, an amplification tag domain, a detection tag domain, and an address tag domain.

17. The method of claim 1, wherein (a), (b), and (c) are performed in a single reaction mixture.

18. The method of claim 1, wherein, wherein the concentration of the one or more proteases in the cell lysate is 22.5 mAU/ml to 90 mAU/ml.

19. The method of claim 1, wherein the one or more proteases comprises a subtilisin.

20. The method of claim 1, wherein the one or more proteases comprises a serine protease, a threonine protease, a cysteine protease, an aspartate protease, a glutamic acid protease, or a metalloprotease.

21. The method of claim 1, wherein the one or more proteases comprises a serine protease.

22. The method of claim 1, wherein the one or more proteases comprises a proteinase K.

23. The method of claim 1, wherein the one or more proteases comprises a heat labile proteinase K.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: a transferred transposon end sequence

<400> SEQUENCE: 1
agatgtgtat aagagacag                                              19

<210> SEQ ID NO 2
<211> LENGTH: 19
<212> TYPE: DNA
<213> ORGANISM: Artificial Sequence
<220> FEATURE:
<223> OTHER INFORMATION: a non-transferred transposon end sequence

<400> SEQUENCE: 2
ctgtctctta tacacatct                                              19
```